US012357782B2

United States Patent
McLaren

(10) Patent No.: US 12,357,782 B2
(45) Date of Patent: Jul. 15, 2025

(54) RESPIRATORY INTERFACE

(71) Applicant: Fisher & Paykel Healthcare Limited, Auckland (NZ)

(72) Inventor: Mark Arvind McLaren, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 1169 days.

(21) Appl. No.: 17/271,347

(22) PCT Filed: Sep. 3, 2019

(86) PCT No.: PCT/IB2019/057393
§ 371 (c)(1),
(2) Date: Feb. 25, 2021

(87) PCT Pub. No.: WO2020/049441
PCT Pub. Date: Mar. 12, 2020

(65) Prior Publication Data
US 2021/0346629 A1 Nov. 11, 2021

Related U.S. Application Data

(60) Provisional application No. 62/726,697, filed on Sep. 4, 2018.

(51) Int. Cl.
*A61M 16/06* (2006.01)
(52) U.S. Cl.
CPC .... *A61M 16/0605* (2014.02); *A61M 16/0666* (2013.01)

(58) Field of Classification Search
CPC .......... A61M 16/0605; A61M 16/0666; A61M 16/047; A61M 16/0633; A61M 16/0683;
(Continued)

(56) References Cited

U.S. PATENT DOCUMENTS 2,917,045 A   12/1958   Schildknecht et al.
5,121,745 A   6/1992   Israel
(Continued)

FOREIGN PATENT DOCUMENTS

WO   WO 2013/050911   4/2013
WO   WO 2015/170997   11/2015

OTHER PUBLICATIONS

International Search Report for Application No. PCT/IB2019/057393 dated Nov. 1, 2019, 5 pages.

*Primary Examiner* — Timothy A Stanis
*Assistant Examiner* — Tina Zhang
(74) *Attorney, Agent, or Firm* — VIA LLP

(57) ABSTRACT

A seal assembly for a respiratory interface, the seal assembly comprising a seal portion configured to form a seal with at least a portion of a user's face, the seal portion comprising a bladder having an internal volume that contains a shear thinning material; and a volume adjuster for adjusting the internal volume of the bladder. Alternatively, the seal assembly comprising a frame; two nasal prongs connected to the frame, each prong comprising a seal portion configured to form a seal with a portion of the user's nares and a flow path extending through the seal portion for delivery of respiratory gas to a user's nare; wherein the seal portion comprises a bladder that contains a shear thinning material.

15 Claims, 26 Drawing Sheets

(58) Field of Classification Search
CPC .. A61M 2205/0288; A61M 2016/0661; A61M 2205/0216; A61M 2207/10; A61M 16/0616; A61M 16/0622; A61M 16/0627; A61M 16/06; A61M 16/0611; A62B 18/08; A62B 18/02–04; A62B 18/025
USPC ............ 128/206.24, 205.25, 206.21, 207.18, 128/206.23, 206.28, 207.13
See application file for complete search history.

(56) References Cited

U.S. PATENT DOCUMENTS

| | | |
|---|---|---|
| 8,852,480 B2 | 10/2014 | Lang et al. |
| 9,078,988 B2 | 7/2015 | Burz et al. |
| 2009/0217929 A1 | 9/2009 | Kwok et al. |
| 2012/0080035 A1* | 4/2012 | Guney .............. A61M 16/0616 128/205.25 |
| 2014/0283832 A1 | 9/2014 | Stegman |
| 2017/0239437 A1* | 8/2017 | Scheirlinck ....... A61M 16/0622 |

* cited by examiner

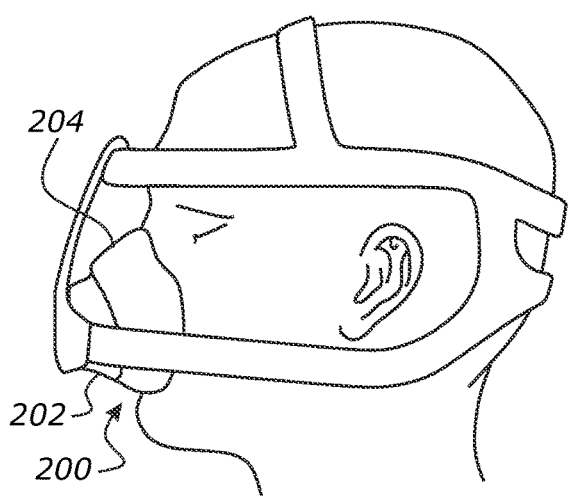
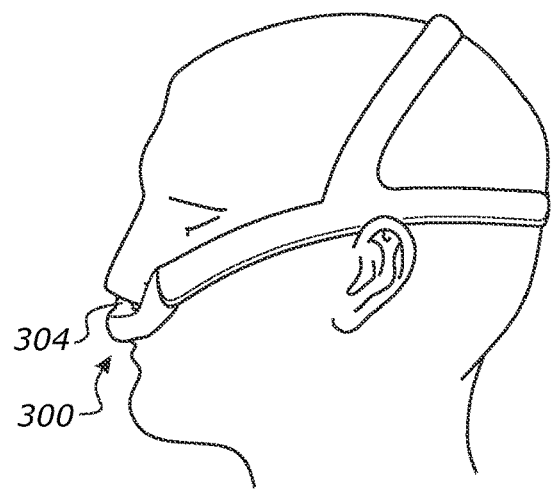
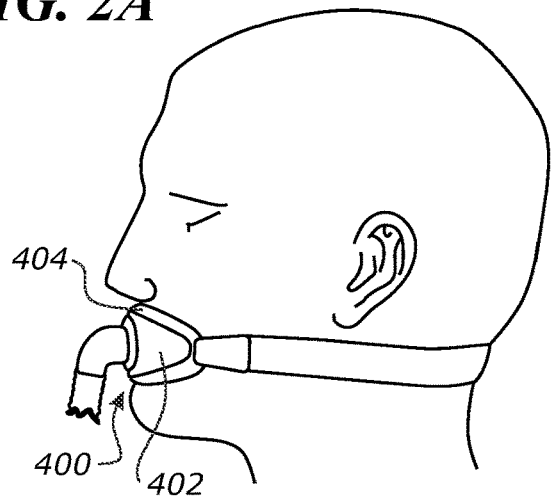
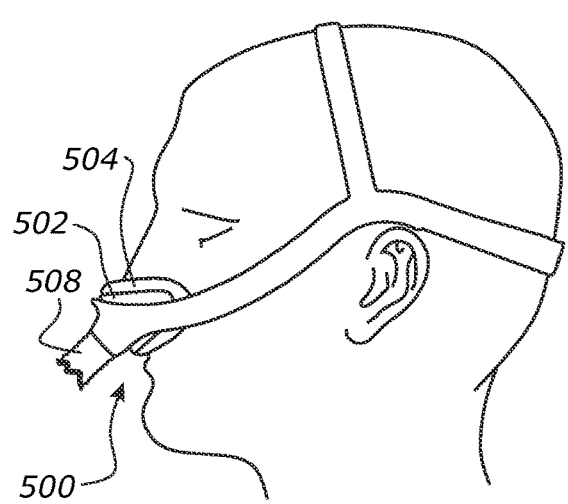
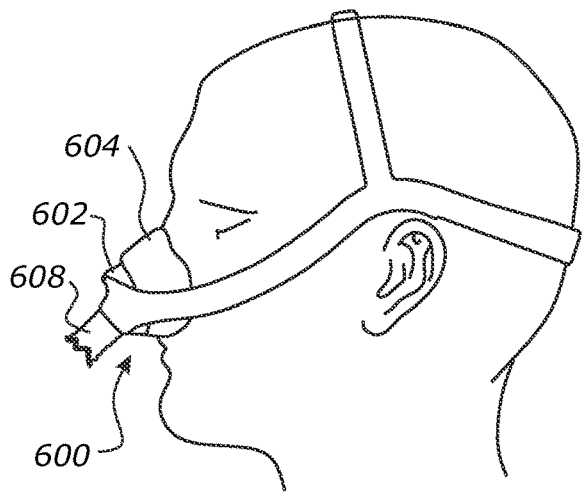
*FIG. 2A*  *FIG. 2B*  *FIG. 2C*  *FIG. 2D*  *FIG. 2E*

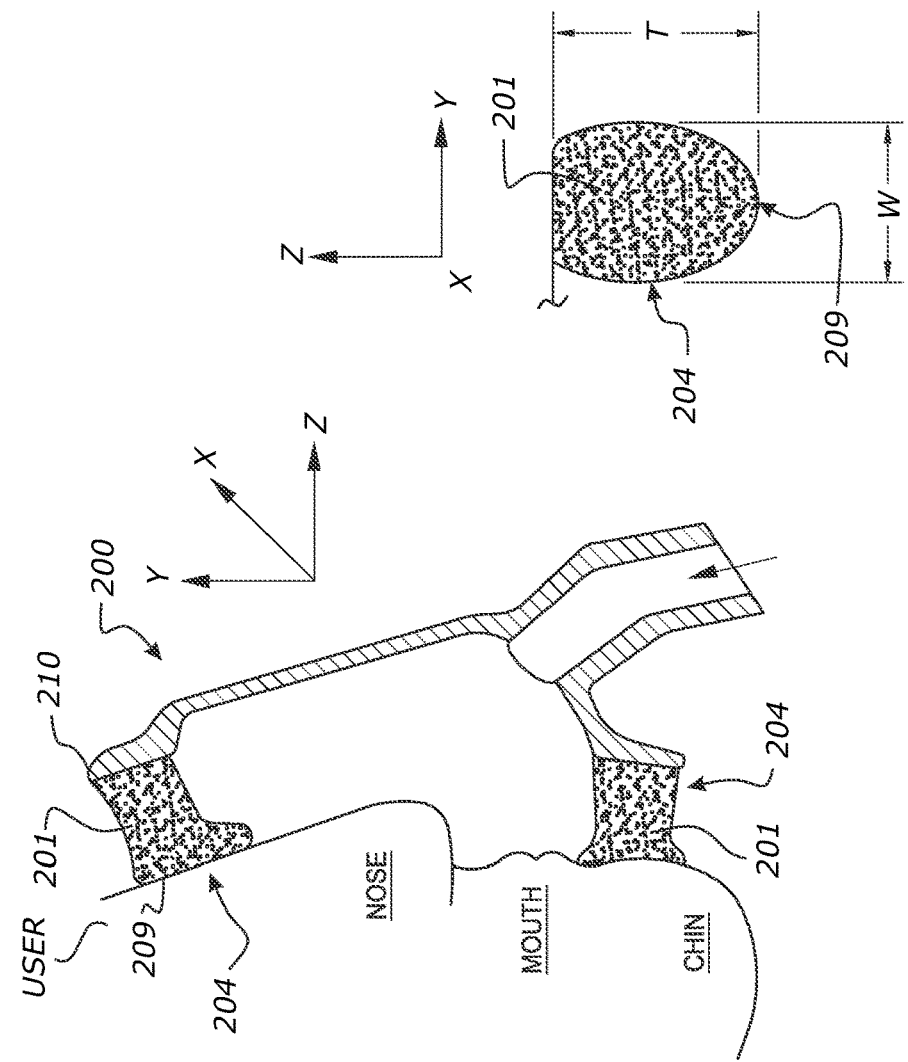
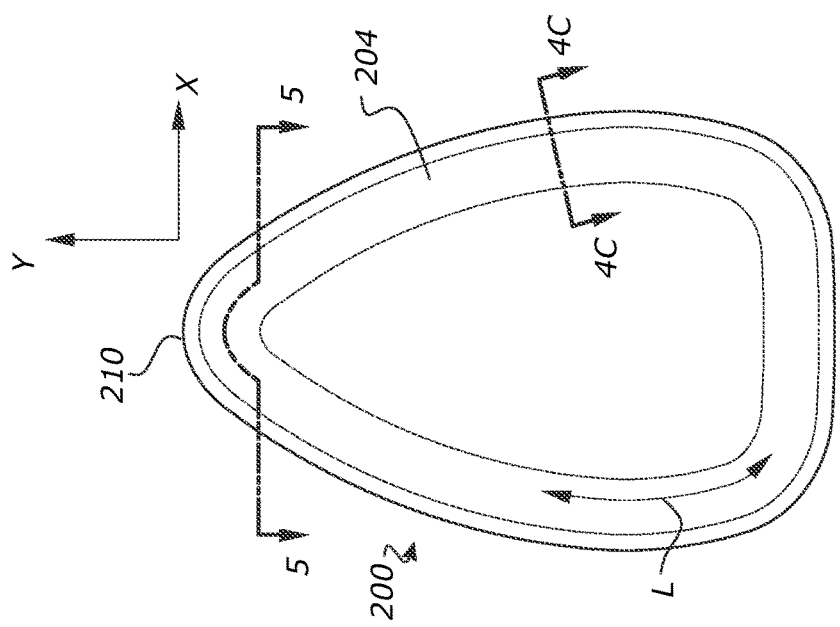
FIG. 4C
FIG. 4B
FIG. 4A

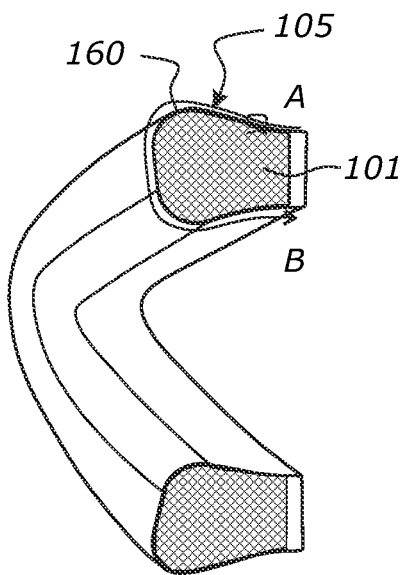
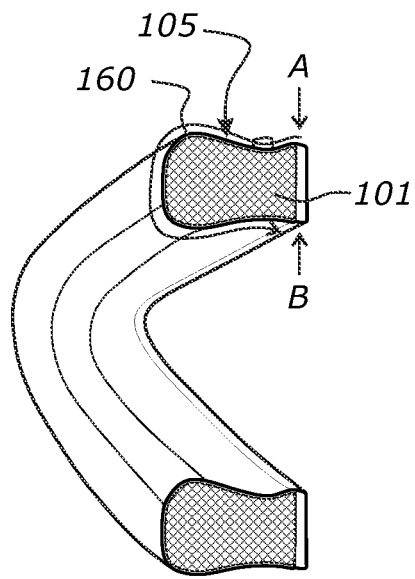
*FIG. 6F*          *FIG. 6G*
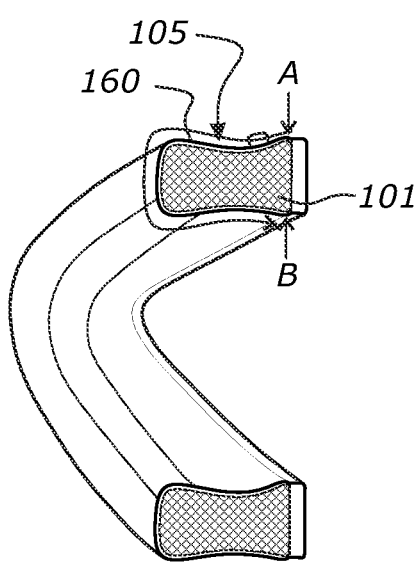
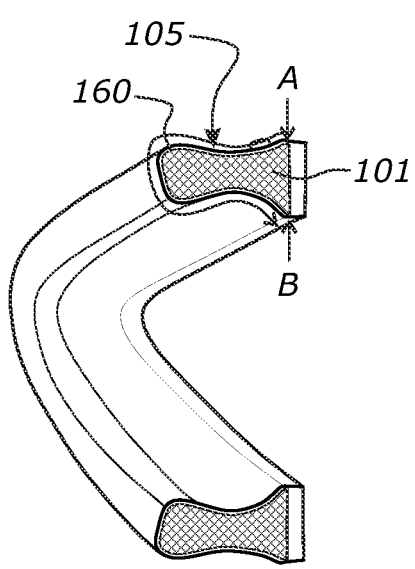
*FIG. 6H*          *FIG. 6I*

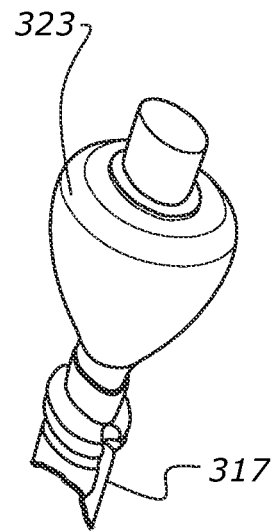
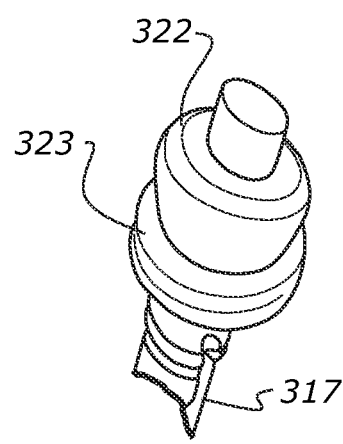
*FIG. 14A*  *FIG. 14B*
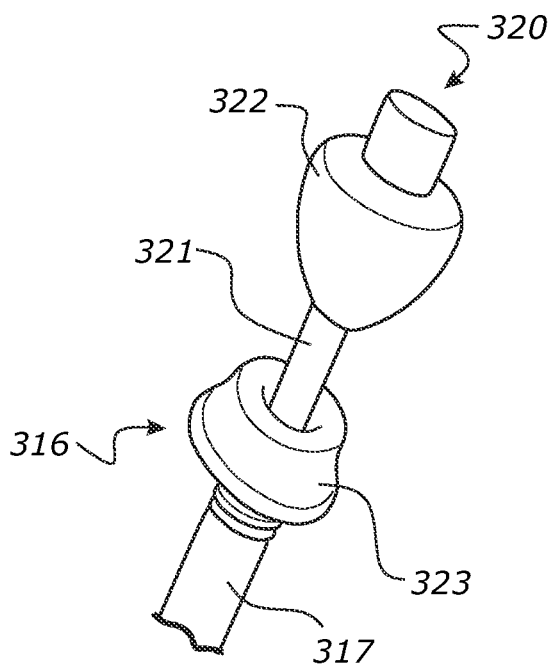
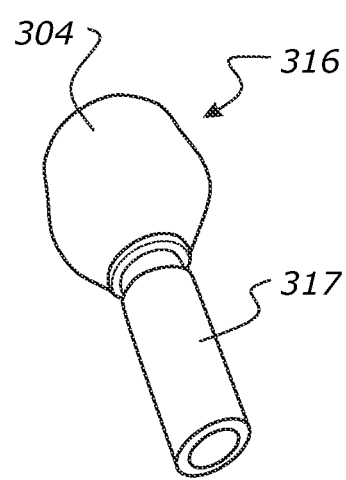
*FIG. 14C*  *FIG. 14D*

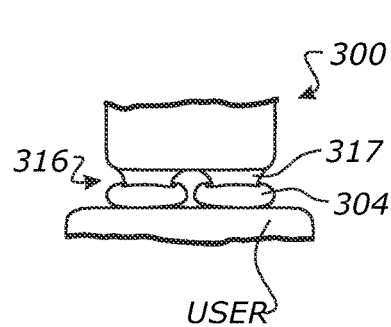
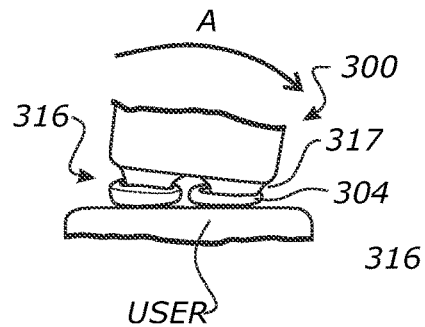
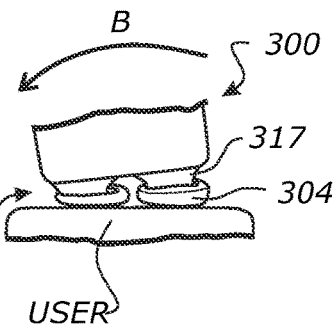
*FIG. 15A*  *FIG. 15B*  *FIG. 15C*
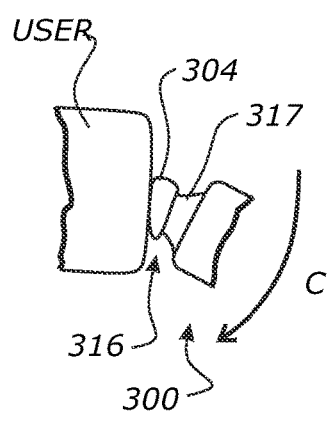
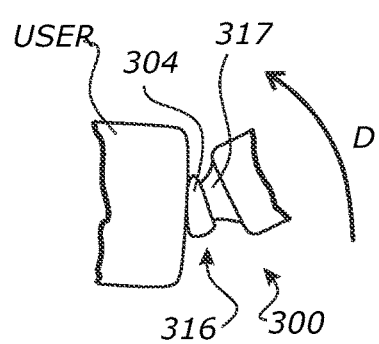
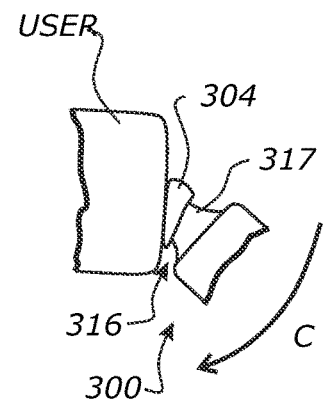
*FIG. 16A*  *FIG. 16B*  *FIG. 16C*

RESPIRATORY INTERFACE

Any and all applications for which a foreign or domestic priority claim is made are hereby incorporated by reference and made a part of the present disclosure.

TECHNICAL FIELD

The present embodiments relate to seal assemblies for respiratory interfaces, including for example, customizable interfaces, and respiratory interfaces comprising such seal assemblies.

DESCRIPTION OF THE RELATED ART

Respiratory interfaces are used for a variety of different therapies, including but not limited to non-invasive ventilation (NIV), oxygen therapy and continuous positive airway pressure (CPAP), for the treatment of various respiratory conditions. Many of these respiratory therapies require that a substantially airtight seal is achieved between an interface and a user. Due to the range of differing facial geometries in the population, it can be difficult to achieve a desired seal as a result of the interface geometry not matching the geometry of a user's face. It is common to apply substantial forces to an interface and user's face in an attempt to overcome any differences in geometry, and achieve a seal. The application of forces to an interface and thus a user's face can cause discomfort as well as injuries to the user, for example at the positions shown in FIGS. 1A and 1B, and are not always successful at attaining satisfactory leak rates.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

It is an object of the present invention to provide a seal assembly for a respiratory interface that overcomes or at least ameliorates some of the abovementioned disadvantages and/or which at least provides the public with a useful choice.

Other objects of the invention may become apparent from the following description which is given by way of example only.

SUMMARY OF THE INVENTION

In one aspect the present invention relates to a seal assembly for a respiratory interface, the seal assembly comprising:
  a seal portion configured to form a seal with at least a portion of a user's face, the seal portion comprising a bladder having an internal volume that contains a shear thinning material; and
  a volume adjuster adapted to adjust the internal volume of the bladder.

In various embodiments the bladder may have an internal resting volume which may be the internal volume of the bladder that is capable of being occupied by the shear thinning material under atmospheric conditions and without modification by the volume adjuster.

In various embodiments the bladder may have an internal resting volume which is the sum of the volume of shear thinning material and a predetermined facial engagement volume. The facial engagement volume may be at least partially filled with gas, or may be partly or substantially evacuated. In such embodiments the facial engagement volume may be a reduced pressure volume or an evacuated volume.

In various embodiments the adjuster is adapted to reduce the bladder to a volume of less than 100% of the internal resting volume.

In various embodiments the shear thinning material may comprise or fill at least about 60, 65, 70, 75, 80, 85, 80, 85, 90, 95, 99, or 100% of the internal resting volume, and useful ranges may be selected between any of these values (for example, about 70 to about 100, about 80 to about 100, about 90 to about 100, about 70 to about 98, about 80 to about 98, about 90 to about 98, about 70 to about 95, about 80 to about 95, about 90 to about 95, about 70 to about 90, or about 80 to about 90%). The balance of the internal resting volume, if any, that is not filled by shear thinning material may comprise the facial engagement volume.

In various embodiments the bladder may be adapted to expand to a volume greater than 100% of a resting volume in use.

In various embodiments the volume adjuster may comprise at least one insertable member configured to be inserted into the bladder to reduce the bladder volume.

In various embodiments the volume adjuster may comprise two insertable members configured to be inserted into the bladder at spaced apart locations to reduce the bladder volume.

In various embodiments the at least one or each insertable member may be slidable within a channel.

In various embodiments the at least one or each insertable member may be adapted to move between a disengaged position in which a substantial portion of the member is outside the bladder and an engaged position in which a substantial portion of the member is inside the bladder.

In various embodiments the at least one or each insertable member may have an engagement surface adapted to be engaged by a user to move the insertable member from a disengaged position to an engaged position.

In various embodiments the volume adjuster may comprise or fill at least about 0.1, 0.5, 1, 2, 3, 4, 5, 6, 7, 8, 9, 10, 11, 12, 13, 14, 15, 20, 25, 30, 35, 40, 50, or 60% of the internal resting volume, and useful ranges may be selected between any of these values (for example, about 0.1 to about 4, about 0.1 to about 6, about 0.1 to about 8, about 0.1 to about 10, about 0.1 to about 15, about 0.1 to about 20, about 0.1 to about 40, about 0.1 to about 50, about 0.1 to about 60, about 2 to about 4, about 2 to about 6, about 2 to about 8, about 2 to about 10, about 2 to about 15, about 2 to about 20, about 2 to about 40, about 2 to about 50, or about 2 to about 60%).

In various embodiments the seal assembly may further comprise at least one flow path through the seal portion for delivery of respiratory gas to the user.

In various embodiments the seal assembly or the seal portion may seal in and/or around the nares of the user, around the mouth or nose of the user, or around the mouth and nose of the user.

In another aspect the invention relates to a seal assembly for a respiratory interface, the seal assembly comprising:
  a frame;
  two nasal prongs connected to the frame, each prong comprising a seal portion configured to form a seal with a portion of the user's nares and a flow path extending through the seal portion for delivery of respiratory gas to a user's nare;

wherein the seal portion comprises a bladder that contains a shear thinning material.

In various embodiments each nasal prong may comprise a stem extending from the frame and through the seal portion, each stem defining the flow path to the user's nare.

In another aspect the invention relates to a respiratory interface comprising a seal assembly described herein; and headgear for holding the seal assembly on a user's face.

The following embodiments may relate to any of the above aspects and embodiments, alone or in any combination.

In various embodiments the bladder may be formed from a flexible, substantially non-elastic material.

In various embodiments the shear thinning material is not an electro-rheological or magneto-rheological fluid.

In various embodiments the shear thinning material may have an exponential relationship between viscosity and shear rate.

In various embodiments the shear thinning material may have a shear stress yield threshold.

In various embodiments the shear thinning material may comprise a Bingham plastic.

In various embodiments the shear thinning material may comprise a pseudoplastic.

In various embodiments the shear thinning material may comprise a pseudo-Bingham plastic.

In various embodiments the shear thinning material may comprise an aqueous composition comprising a metal salt or metalloid salt and at least one polyol.

In various embodiments the metal salt or metalloid salt may be selected from the group consisting of aluminium hydroxide, calcium carbonate, calcium hydrogen phosphate, silica, zeolite and hydroxyapatite, or a combination of any two or more thereof.

In various embodiments the least one polyol may be selected from the group consisting of glycerol, sorbitol, xylitol, 1,2-propylene glycol and polyethylene glycol, or a combination of any two or more thereof.

In various embodiments the shear thinning material may comprise xanthan gum.

In various embodiments the shear thinning material may have a shear thinning index useful herein, such as may be determined according to ASTM E3070-16.

In various embodiments the shear thinning material may have a minimum viscosity of 275,000 cP and a maximum viscosity of 1,550,000 cP at 2 rpm, and a minimum viscosity of 100,000 cP and a maximum viscosity of 550,000 cP at 12 rpm, as determined at 23° C. using a Fungilab S. A. ViscoStar+ R viscometer with a PF T bar spindle and a 70 mL sample container having a diameter of 41 mm and a height of 53 mm on a Heldal helical path stand, the container comprising 70 mL of shear thinning material, where the spindle is lowered into the sample container at a rate of $3.70 \times 10^{-4}$ m/s.

In various embodiments the shear thinning material may have an exponential relationship between viscosity and shear rate between 2 rpm and 12 rpm, as determined at 23° C. using a Fungilab S. A. ViscoStar+ R viscometer with a PF T bar spindle and a 70 mL sample container having a diameter of 41 mm and a height of 53 mm on a Heldal helical path stand, the container comprising 70 mL of shear thinning material, where the spindle is lowered into the sample container at a rate of $3.70 \times 10^{-4}$ m/s.

In various embodiments the shear thinning material may be adapted to redistribute around the facial geometry of the user in use.

In various embodiments the bladder may be a continuous chamber throughout the seal portion.

In various embodiments the seal portion may comprise two or more, or three or more bladders.

In various embodiments when breathable gas is supplied to the user at 20 cmH$_2$O, less than 5 N, or less than 4 N of blow-off force is applied to the headgear used to hold the seal portion to the user.

In various embodiments the headgear may comprise two side straps connected above and behind the user's ears to a rear strap configured to extend across the occiput of the user's head.

In various embodiments the headgear may further comprise a top strap provided to the side straps and configured to extend across the parietal region of the user's head.

In various embodiments the side straps may be removably connected to the seal assembly.

In various embodiments the side straps may be removably connected to the seal assembly by a connector, such as a hook and loop, snap lock, click fit, or magnetic connector.

As used herein the term "and/or" means "and" or "or", or both.

As used herein "(s)" following a noun means the plural and/or singular forms of the noun.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

The term "comprising" as used in this specification means "consisting at least in part of". When interpreting statements in this specification which include that term, the features, prefaced by that term in each statement or claim, all need to be present but other features can also be present. Related terms such as "comprise" and "comprised" are to be interpreted in the same manner.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The invention will now be described by way of example only and with reference to the drawings in which:

FIGS. 2A-2E show a series of different respiratory interfaces in accordance with embodiments of the invention.

FIG. 4A is a schematic front elevational view of the seal portion 204 of a seal assembly 200 in accordance with an embodiment of the invention.

FIG. 4B is a partial side elevational and cross-sectional view of the seal portion 204 of FIG. 4A applied to a user.

FIG. 4C is an enlarged schematic cross section view of a portion of the seal portion 204 illustrated in FIG. 4A taken along line 4C-4C.

FIGS. 6A to 6I show a process for the manufacture of various seal portions in accordance with an embodiment of the invention. FIG. 6A shows an empty bladder of a seal portion that is in the process of being filled with shear thinning material. FIGS. 6B to 6E show the bladder of FIG. 6A substantially 100% filled, about 75% filled, about 50% filled and about 25% filled with shear thinning material respectively. FIGS. 6F to 6I show the bladders of FIGS. 6B to 6E respectively, after the evacuation of air from the bladder and after the bladder is sealed.

FIGS. 14A-14D illustrate a method of making a nasal prong 316 of a seal assembly 300 according to an embodiment of the invention.

FIGS. 15A-15C illustrate the range of angular adjustment that the nasal prong 316 embodiment of FIGS. 12 and 13 may be able to accommodate while providing a satisfactory seal due to the ability of the shear thinning material to redistribute within the seal portion 304 of the prongs 316 as required.

FIGS. 16A-16C illustrate different approach angles of the nasal prong 316 of a seal assembly 300 according to one embodiment and the ability of the shear thinning material to redistribute around the seal portion of the prong as required.

FIG. 21A illustrates the seal portion 204 in a neutral state and FIG. 21B illustrates the seal portion 204 when sealed with a portion of a user's face.

FIG. 22A shows the seal portion of the seal assembly in a neutral state and FIG. 22B shows the seal portion when sealed with a portion of a user's face.

DETAILED DESCRIPTION OF THE INVENTION

The embodiments described below are described in the context of therapeutic fluid delivery devices which include seals designed to form seals with areas of patients encircling a target treatment area. However, the inventions disclosed herein can be applied to other devices designed for uses in other environments, including devices for non-medical uses, and uses on non-humans, and/or inanimate objects.

Interface Features

Figure 1A:
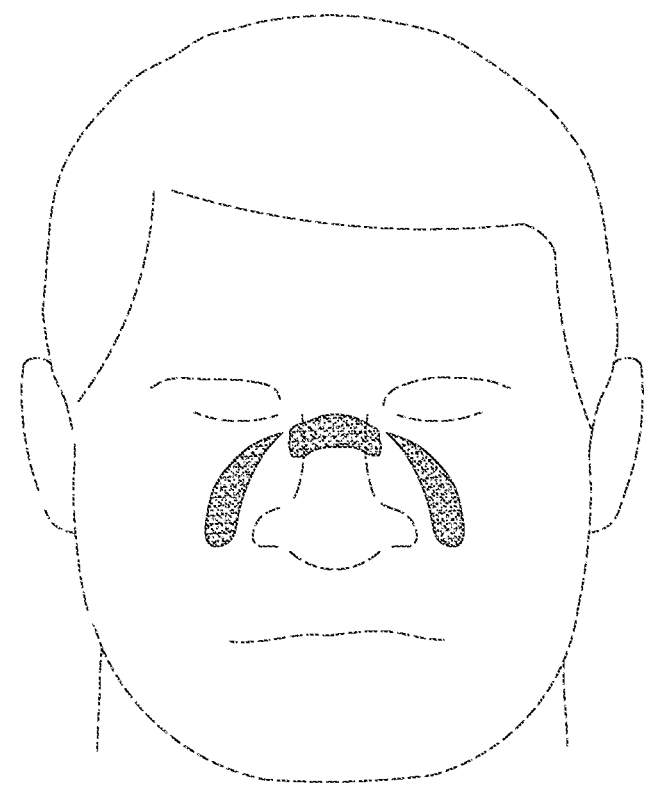
FIGS. 1A and 1B are schematic front elevational views of patient faces showing areas of injuries caused by seal assemblies of known respiratory interfaces.
Figure 1B:
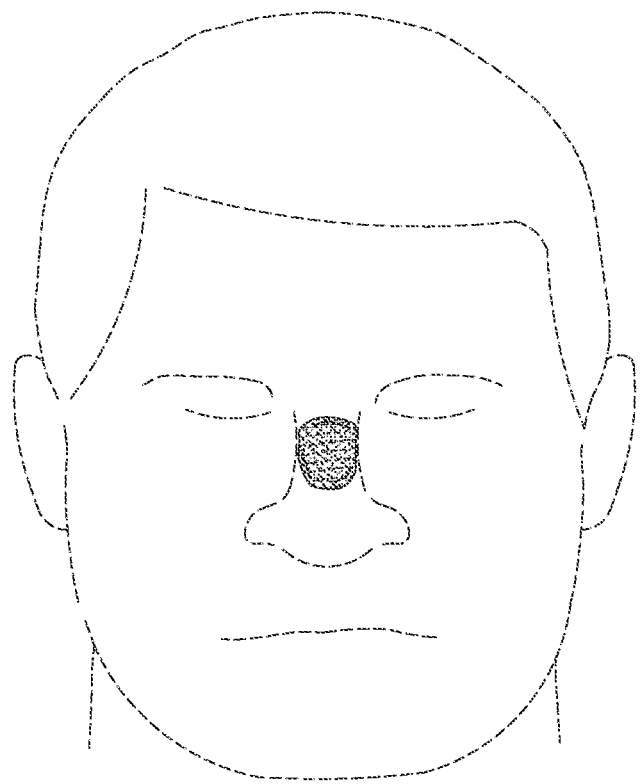
Figure 1C:
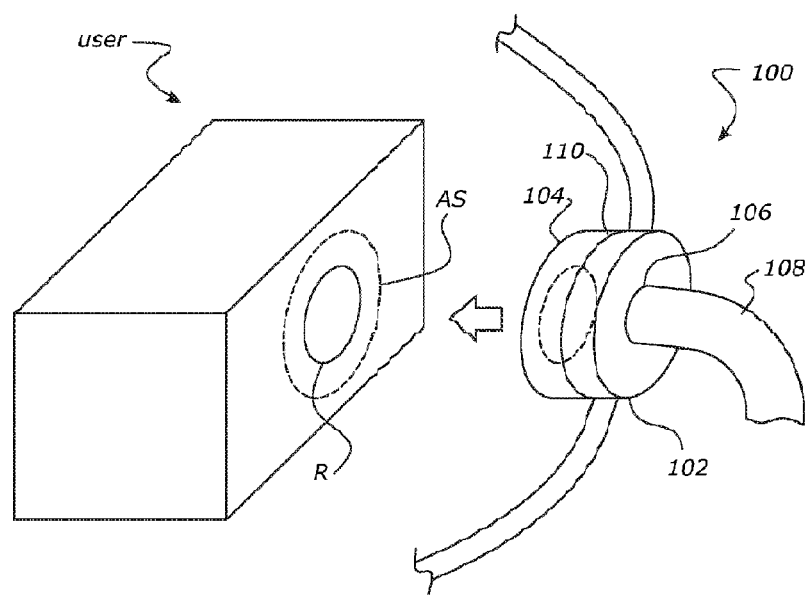
FIG. 1C is a schematic perspective and exploded view of a patient and a respiratory interface in accordance with an embodiment of the invention.

FIG. 1C schematically illustrates the seal assemblies of the invention using the reference numeral 100. The seal assemblies 100 comprise a shear thinning material which provides improved compatibility with differently-shaped contours of a user or patient. Throughout the specification, any reference to seal assembly 100 and components of seal assembly 100 (labelled using the 100 series) is intended to be a general reference to all seal assemblies of the invention.

With reference to FIG. 1C, seal assembly 100 comprises a housing portion 102 comprising a conduit connection portion 106 and a seal portion 104. The seal portion 104 comprises a sealing surface and a connecting portion being connected to the housing portion 102.

With reference to FIG. 1C seal assemblies of the invention can be configured for providing a sealing arrangement with respect to a target area R of a patient to be treated with the seal assembly. For example but without limitation, the target area R may be an area of the patient's body, such as the patient's skin, with an undesirable characteristic, such as disease, an incision, a wound, or one or any combination of a patient's respiratory orifices, such as one or both nostrils (e.g., nasal masks), the mouth (oral masks), tracheotomy incisions, as well as other types of wounds, incisions, orifices, or areas to be treated with the seal assembly. As such, seal portion 104 can be configured to generate a seal with an area or portion of the patient AS surrounding any one or any combination of the target areas R noted above. The portion AS can be in the form of skin, hair, with or without or other structures intended to be left in place during use of the seal assembly 100, such as a nasogastric tube.

With continued reference to FIG. 1C, the seal portion 104 of the seal assembly 100 also comprises at least one flow path through the seal portion for fluid communication with a target area of a user, for example for fluid communication of the user's airway with a conduit 108, such as an air conduit, supplying a source of breathable gas to a user. For example, but without limitation, in embodiments where the seal assembly is in the form of a pillow-type nasal mask, the seal portion can be in the form of a bulbous member configured to generate seals around the nares of a patient's nose. In such embodiments, the patient's nares corresponds to the respiratory orifice R of FIG. 1C and the skin tissue surrounding the patient's nares corresponds to the area AS of FIG. 1C. Known nasal-type seal assemblies are commercially available in various forms, including the Pilairo Q and Opus 360 masks available from Fisher & Paykel Healthcare.

With continued reference to FIG. 1C, the housing portion 102 of seal assemblies 100 of the invention can be substantially rigid. Thus, the seal portion 104 may provide more flexibility for following the contours of the user's face so as to provide the desired seal during use. More particularly, the seal portion 104 may be configured to form a substantially airtight connection with both the housing portion 102 as well as the skin surrounding the patient's nose and/or mouth. The connection between the housing portion 102 and the seal portion 104 can be permanent or detachable.

With reference to FIG. 1C, the conduit connection portion 106 can be in the form of a connection for receiving or discharging fluids. For example, the conduit connection portion 106 can be in the form of a respiratory conduit connection adapted to deliver a flow of breathable gas to a patient, which can optionally be incorporated into an aperture of the housing portion 102 to provide connection to a respiratory air conduit. The air conduit 108 can be of the type for supplying a flow of pressurized breathable gases to a user through a flow path in the seal portion 104 of seal assembly 100.

FIGS. 2A-2E illustrate some embodiments of the seal assembly 100, identified by reference numerals 200, 300, 400, 500 and 600 respectively. Parts, components and features of these interfaces which are similar or the same as corresponding parts or features of the generic interface 100 are identified by the same reference numeral in subsequent figures except that a value of 100, 200, 300, 400 or 500 has been added thereto as appropriate.

With reference to FIGS. 2A-2E, seal assembly 100 may be configured to extend over and form a seal with the skin surrounding a patient's nose and mouth in a full-face seal assembly 200 (FIG. 2A), a patient's nostrils with prongs or pillows in a nasal seal assembly 300 (FIG. 2B), a patient's mouth in an oral seal assembly 400 (FIG. 2C), the underside of a patient's nose, with or without an exposed tip of a patient's nose in seal assembly 500 (FIG. 2D), or the nose of a patient including the nasal bridge in seal assembly 600 (FIG. 2E). Other configurations may also be used.

In some embodiments the seal assembly may be incorporated into a full face under nose mask. It will be understood by a person skilled in the art that the seal assembly of the invention may be incorporated into more than one part of a full face under nose mask. For example, in some embodiments the seal assembly may be incorporated into the part of a mask or interface that is adapted to seal under the nose and/or around the nostrils of a user. In some embodiments the seal assembly may be incorporated into a part of the mask or interface adapted to seal around the mouth of a user. In some embodiments the seal assembly may be incorporated into both the part of the mask or interface adapted to seal under and/or around the nostrils of a user and around the mouth of a user.

In some embodiments, the mask or interface, for example, a full face under nose mask, may comprise more than one seal assembly, each seal assembly comprising its own volume adjuster, or pair of volume adjusters. In some embodiments, the mask or interface, such as a full face under nose mask, may comprise more than one seal assembly and the more than one seal assembly may share one volume adjuster.

Figure 3A:
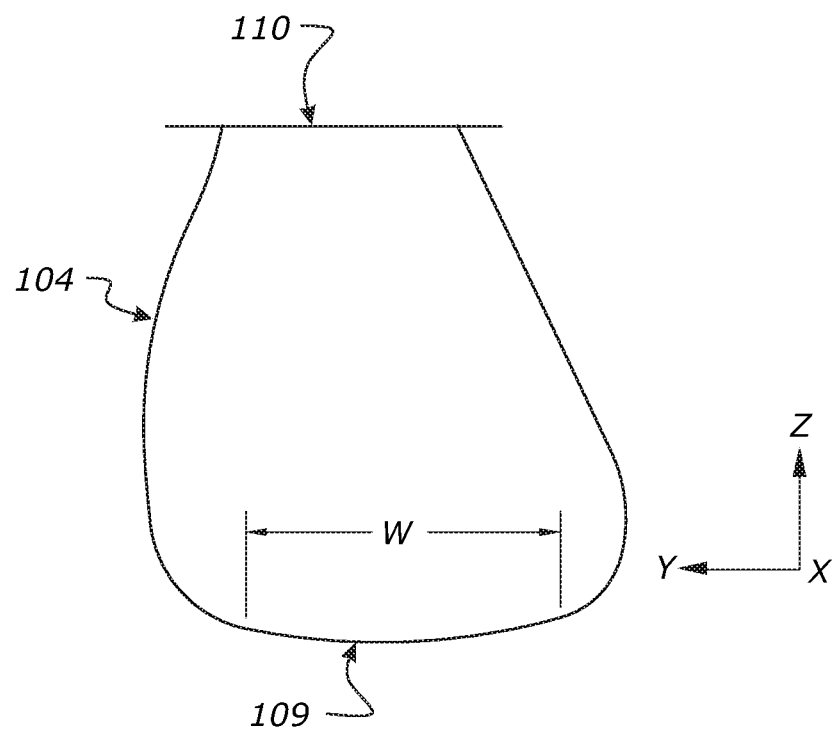
FIGS. 3A and 3B are schematic cross sectional views of a seal portion 104 of a seal assembly 100 according to an embodiment of the invention, illustrating that the seal portion 104 has a width (W) that may be enlarged when the seal assembly 100 is donned by a user (FIG. 3B) compared to the width (W) before donning (FIG. 3A).
Figure 3B:
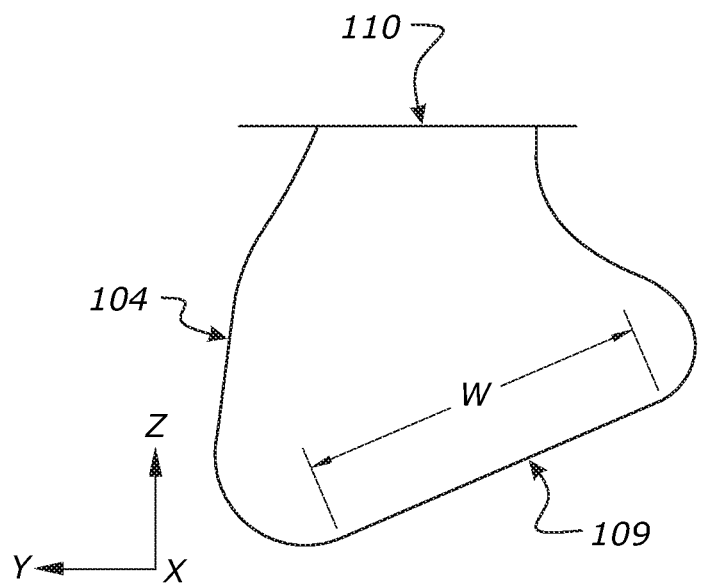

The seal portions of the seal assemblies described herein comprise a portion intended to extend over a target area R of a patient at a sealing surface having a width and length. With reference to FIGS. 3A and 3B and using generic seal assembly 100 as an example, the term "width of the sealing surface" as used herein is intended to refer to the width of the sealing surface 109 of the seal portion 104 measured in direction "W". The sealing surface is the area or portion of the seal that contacts the patient's skin in use.

Referring again to FIGS. 3A and 3B, and continuing to use generic seal assembly 100 as an example only, the sealing surface 109 or "face" of the seal portion 104 is the portion of the seal portion 104 that is most proximal to the face of the patient, in the Z-axis direction. Portions of the sealing face 109 might approximately lie in the X-Y plane when in a neutral or relaxed state. In some embodiments the sealing surface 109 may move from the neutral or relaxed state (FIG. 3A) to a conformed state in which the sealing surface 109 may be distorted out of the X-Y plane (FIG. 3B) in the process of conforming to the contours of a user's face. Seal assemblies deformed as such, may be secured to a user's face, for example, with typical head straps, to attempt to provide a more continuous and even-pressured seal around one or more respiratory orifices of a patient, for example, part or all of the nose and/or mouth of a patient. As such the seal assemblies and interfaces comprising seal assemblies according to the invention may provide at least one of the following, or other, benefits:

- alleviation of pressure points by allowing seal assembly retention forces to be spread evenly over the seal assembly,
- the seal portion may be less likely to collapse and allow the housing portion (if present) to bottom-out on the user's face,
- reduced skin pressure during use,
- reduced leaks during use,
- reduced occurrences of shear force being applied to the face,
- reduced blow-off force,
- ability to create a seal with varying headgear forces to achieve a loose to tight fit, conforms to a patient's facial geometry without creating a resulting spring force in the seal portion (which is an inherent issue in elastomeric seals), improved seal as a result of the seal portion being able to conform to varying facial geometries and actively reshaping as a user's face shape changes during use, improved stability as the seal portion is in a higher viscosity state at rest, improved patient compliance, a range of arrangements (tight-fit and loose-fit), minimized mask leakage, reduced mechanical deformation forces in the seal portion, the ability to semi-customize the seal assemblies and/or interfaces for a user, improved user comfort, improved adjustability, and/or improved conformance to components such as nasogastric tubes.

An additional advantage of the seal assemblies of the invention is that while in storage, the seal portion of the seal assembly remains in a moulded state that matches the facial geometry of the last user, improving the ease of donning.

The deformation of the seal portion described above with reference to seal assembly 100 is also shown in FIGS. 4A-4C using seal assembly 200. FIG. 4A illustrates that in some areas along the length "L" (FIG. 4A) of the seal portion 204, the width W of the sealing surface 209 can lie generally in the X-Y plane identified in FIG. 4C, for example, when the seal portion 204 is a neutral state. However, other portions of the sealing surface 209 can extend into the Z-axis. For example, when the seal portion 204 is adjusted or conformed to a user's face, the orientation of the sealing surface 209 may change such that the sealing surface 209 extends along the Z-axis as well (see FIG. 4B).

The term "thickness of the seal portion" is intended to refer to the dimension labelled as "T" in FIG. 4C. The thickness T of the seal portion 204 extends in the Z-dimension identified in FIG. 4B.

Continuing to user interface 200 as an example only, and with reference to FIG. 4A, the term "length of the seal portion" is intended to refer to the length L of the seal portion 204 as measured around the periphery 210 of the seal assembly 200. The length L of the seal portion 204 does not normally extend only along a single plane and thus would normally extend along a "3-Dimensional" path around the periphery 210 of the seal assembly 200.

It will be understood by a person skilled in the art that the above descriptions of "W", "T" and "L" may also be applicable to a number of other seal assemblies of the invention, not just the full face embodiment 200 shown in FIGS. 2A and 4A-4B.

Nature of the Shear Thinning Material

In various embodiments the present invention relates to seal assemblies comprising a seal portion, the seal portion comprising at least one shear thinning material.

In some embodiments the seal portion may be formed nearly entirely with materials or mechanisms that can be transitioned between different states of viscosity.

The shear thinning materials in the seal assemblies of the invention transition from a state of higher stiffness or higher viscosity (stiffer, hardened, rigid) to a state of reduced stiffness or reduced viscosity (e.g., flowable, flexible, conformable) at a particular shear stress yield threshold, the shear stress yield threshold being dependent on the material.

The inventors have found that various shear thinning materials may be used in accordance with the invention, in particular shear thinning materials with a shear thinning index useful herein, such as may be determined according to ASTM E3070-16.

In some embodiments the shear thinning materials may be selected from various non-Newtonian fluids, for example Bingham plastics, pseudoplastics, and pseudo-Bingham plastics. In various embodiments the shear thinning material is not an electro-rheological or magneto-rheological material.

Suitable shear thinning materials may be, for example aqueous compositions comprising a metal salt or metalloid salt and at least one polyol.

In some embodiments the metal salt or metalloid salt may be selected from the group consisting of aluminium hydroxide, calcium carbonate, calcium hydrogen phosphate, silica, zeolite and hydroxyapatite, or a combination of any two or more thereof, and the at least one polyol may be selected from the group consisting of glycerol, sorbitol, xylitol, 1,2-propylene glycol and polyethylene glycol, or a combination of any two or more thereof.

In some embodiments the shear thinning material comprises xanthan gum.

In various embodiments the shear thinning material may have one or more of the following attributes:

a stable moisture content to allow the material to maintain its shear thinning behaviour, a light weight, low or no odour, and biocompatibility, including acceptable thermal properties.

Using the previously described dimensional labels for reference, in some embodiments, the shear thinning material of the seal portion can extend along only a portion of the longitudinal length L of the seal portion or along the entire length L of the seal portion.

Location and Nature of Shear Thinning Material

The shear thinning portion of a seal assembly is the part of the seal portion comprising a shear thinning material. In some embodiments the shear thinning portion may extend substantially along the entire width W of the seal portion of an interface. As used herein, the phrase "substantially an entire width of the seal portion" is intended to mean at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.9, or 100% of the width W of the seal portion and useful ranges may be selected from any of these values, for example from about 60 to about 70, from about 60 to about 75, from about 60 to about 80, from about 60 to about 85, from about 70 to about 75, from about 70 to about 80, from about 70 to about 85, or from about 60 to about 100% of the width of the seal portion.

In some embodiments, the entire seal portion may comprise a shear thinning material. In some embodiments the shear thinning material may comprise or fill at least about 60, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.9, or 100% of an internal resting volume of the seal portion and useful ranges may be selected from any of these values, for example about 60 to about 70, about 60 to about 75, about 60 to about 80, about 60 to about 85, about 60 to about 90, about 60 to about 95, about 60 to about 100, about 70 to about 80, or about 70 to about 85, about 70 to about 90, about 70 to about 95, about 70 to about 100, about 75 to about 80, about 75 to about 85, about 75 to about 90, about 75 to about 95, about 75 to about 100, about 80 to about 90, about 80 to about 95, about 80 to about 100, about 90 to about 100, about 60 to about 98, about 70 to about 98, about 80 to about 98, about 90 to about 98, about 60 to about 95, about 70 to about 95, about 80 to about 95, or about 90 to about 95%. The proportion of the shear thinning material to the overall size of the seal portion may depend on various factors, for example, a predetermined facial engagement volume of the seal portion, where present. The predetermined facial engagement volume is described in more detail below.

In some embodiments, the shear thinning material of the seal portion can be in the form of one or more layers within the seal portion. In some embodiments, the one or more layers may comprise one or more of the same or different shear thinning materials.

In some embodiments the seal portion may be made up of two or more or three or more pockets or compartments, some or all of which may comprise a shear thinning material, such that at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.9, or 100% of the total volume of the seal portion comprises shear thinning material and useful ranges may be selected from any of these values, for example about 60 to about 70, about 60 to about 75, about 60 to about 80, about 60 to about 85, about 60 to about 90, about 60 to about 95, about 60 to about 100, about 70 to about 80, or about 70 to about 85, about 70 to about 90, about 70 to about 95, about 70 to about 100, about 75 to about 80, about 75 to about 85, about 75 to about 90, about 75 to about 95, about 75 to about 100, about 80 to about 90, about 80 to about 95, about 80 to about 100, about 90 to about 100, about 60 to about 98, about 70 to about 98, about 80 to about 98, about 90 to about 98, about 60 to about 95, about 70 to about 95, about 80 to about 95, or about 90 to about 95%.

In some embodiments, the shear thinning material may be present in a bladder, for example a bladder located within the seal portion. In some embodiments the bladder may be a space or void within the seal portion. In some embodiments the bladder may be formed from a flexible, substantially non-elastic material, for example a medical grade polymer.

The bladder may comprise part of the seal portion, that is, the bladder and the seal portion may be one and the same. In some embodiments the bladder may be a continuous chamber within and throughout substantially the entire seal portion. In some embodiments the seal portion may comprise multiple bladders, each bladder forming a compartment within the seal portion. The bladder may be in the form of a chamber, particularly an airtight chamber comprising at least about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.9, or 100% of the total volume of the seal portion and useful ranges may be selected from any of these values, for example about 60 to about 70, about 60 to about 75, about 60 to about 80, about 60 to about 85, about 60 to about 90, about 60 to about 95, about 60 to about 100, about 70 to about 80, or about 70 to about 85, about 70 to about 90, about 70 to about 95, about 70 to about 100, about 75 to about 80, about 75 to about 85, about 75 to about 90, about 75 to about 95, about 75 to about 100, about 80 to about 90, about 80 to about 95, about 80 to about 100, about 90 to about 100, about 60 to about 98, about 70 to about 98, about 80 to about 98, about 90 to about 98, about 60 to about 95, about 70 to about 95, about 80 to about 95, or about 90 to about 95.

In various embodiments the bladder is positioned within the seal portion at or proximate to the portions of the seal portion which contact the area AS of a user.

In various embodiments the seal assembly may comprise a volume adjuster adapted to adjust the internal resting volume of the bladder. For example, the volume adjuster may comprise an insertable member such as a piston, configured to be inserted into the bladder to reduce the bladder volume.

In various embodiments the volume adjuster may comprise two or more insertable members, for example 2, 3, 4, 5, 6, 7, 8, 9, 10 or more insertable members, preferably two insertable members.

In various embodiments the volume adjuster is adapted to reduce the bladder to a volume of less than 100% of the internal resting volume, for example less than 99, 98, 97, 96, 95, 90, 85, 80, 75, 70, 65, 60, 55, 50, 45 or 40% of the internal resting volume, and suitable ranges may be selected from any of these values for example less than about 100 to about 40%, less than about 100 to about 60% or less than about 100 to about 80% of the internal resting volume.

The one or more volume adjusters may be slidable within a channel, for example a channel in the seal portion, such that the insertable member is adapted to move between a disengaged position in which a substantial portion of the member is outside the bladder and an engaged position in which a substantial portion of the member is inside the bladder.

Alternative mechanisms that adjust the internal resting volume of the bladder are also contemplated. For example, a fluid that is substantially incompressible under operating conditions may be introduced into the bladder, directly into the bladder or into a second bladder that is nested within the first bladder. In a further alternative, a restricting band may be applied to the exterior of the bladder, reducing the effective external area of the bladder and so reducing its internal volume. In yet another alternative, the bladder further comprises a reservoir in fluid communication with the bladder, where the interior volume of the reservoir may be reduced so as to reduce the overall internal volume of bladder and reservoir in combination.

The volume adjuster may comprise a pair of volume adjusters, such as a pair of insertable members, for example a pair of pistons. In some embodiments the pair of volume adjusters may be configured to be insertable into the bladder at spaced apart locations (for example, as shown in FIG. 5) to reduce the bladder volume.

Figure 5A:
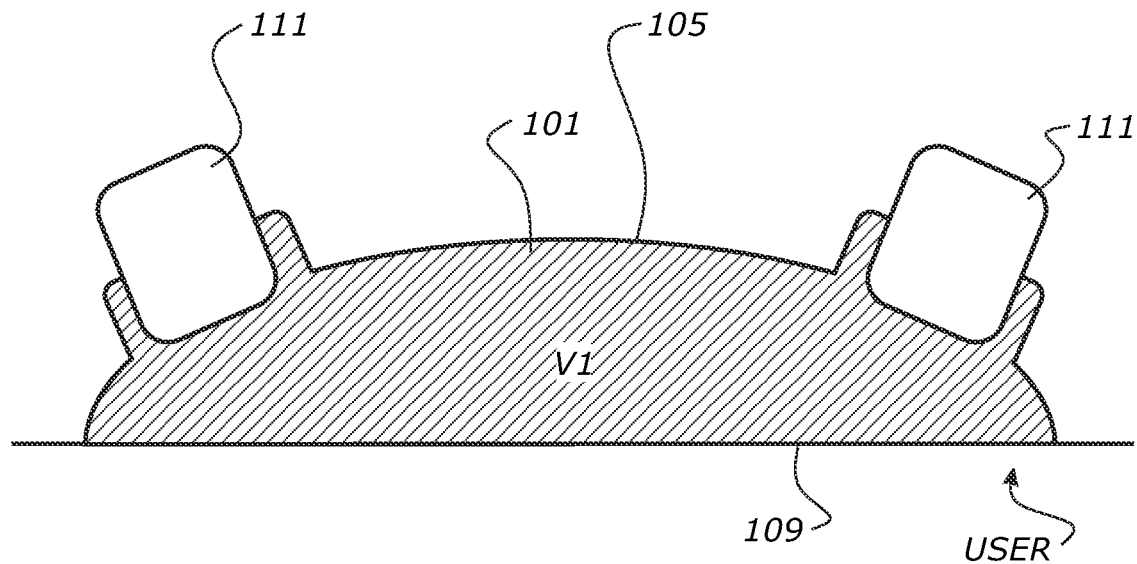
FIGS. 5A and 5B are schematic cross-sectional views of a volume adjuster 111 of a seal assembly 100 in a disengaged position in which a substantial portion of the volume adjuster 111 is outside the bladder 105 (FIG. 5A), and in an engaged position in which a substantial portion of the volume adjuster 111 is inside the bladder 105 (FIG. 5B) in accordance with an embodiment of the invention.
Figure 5B:
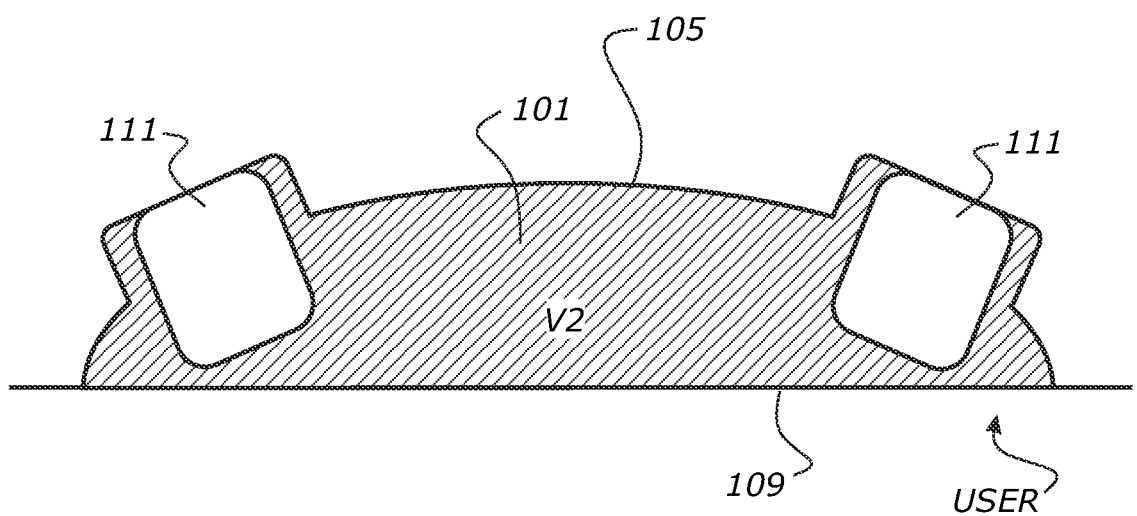

FIG. 5A shows a seal assembly 100 according to an embodiment of the invention, with a seal portion comprising a bladder 105 of volume V1 and comprising a shear thinning material 101. In FIG. 5A, the insertable members (pistons) 111 are located in a disengaged position substantially outside the bladder 105. FIG. 5B shows that the volume of the bladder 105 is reduced to a volume V2 when pistons 111 are moved inside the bladder 105 to an engaged position. In embodiments comprising a facial engagement volume (discussed below), V1 may be the sum of the shear thinning material volume and the facial engagement volume.

It will be understood by a person skilled in the art that the terms "substantially inside", "substantially outside" and a "substantial part" when used in reference to the insertable members may encompass a range of embodiments in which a "substantial part" comprises at least 10, 20, 30, 40, 50 60, 70, 80, 90 or more, for example 100% of the insertable member, and useful ranges may be selected from any of these values. For example, FIG. 5A shows a seal assembly 100, in which the insertable members 111 are in a disengaged position. In this embodiment the term "a substantial part" corresponds to approximately 50% of the insertable member 111. With reference to FIG. 5B, the seal assembly 100 of FIG. 5A is shown in an engaged position. In this embodiment, the "substantial part" of the insertable member 111 corresponds to 100% of the insertable member.

It will be understood by a person skilled in the art that the volume adjuster 111 shown in FIGS. 5A and 5B may be incorporated into a range of different seal assemblies as described herein, for example full-face assemblies 200, around the mouth assemblies 400, around/under nose assemblies 500 and 600 and nasal assemblies 300.

In some embodiments the reduced volume of the bladder achieved using a volume adjuster may lead to an increase in the internal pressure of the bladder, causing the shear thinning material within the bladder to spread out across the sealing surface of the seal assembly, leading to an improved seal and conformability.

The volume adjuster may comprise an engagement surface adapted to be engaged by a user. For example, the volume adjuster may comprise one or more insertable members as described above, and at least one or each insertable member may have an engagement surface adapted to be engaged by a user to move the insertable member from a disengaged position to an engaged position.

In some embodiments the volume adjuster may be manually-operable. For example, as described herein a user may be able to move the volume adjuster by pushing down on the engagement surface of the volume adjuster, such as a piston or pair of pistons, to move them from a disengaged position to a partly or fully engaged position. The volume adjuster may be operated once the seal assembly and the interface and headgear are donned by a patient, to achieve a more effective and comfortable seal.

The engaged position may be selected from one or more predetermined positions that the volume adjuster, for example the insertable member can slide and lock into. For example, the one or more volume adjusters may be able to slide and lock into one of a number of predetermined engaged positions, for example 2, 3, 4, 5, 6, 7, 8, 9, 10 or more predetermined partly engaged positions. In some embodiments there may be only one predetermined engaged position that the one or more volume adjusters can slide and lock into.

In some embodiments the seal assembly may not comprise predetermined positions that the volume adjuster, for example the insertable member can slide and lock into. The insertable member may be slideable within a channel and may be lockable at any position within the channel.

The volume adjuster may further comprise a release mechanism, for example, a button for returning the piston or pistons to a disengaged position. Other techniques can also be used.

In some embodiments the volume adjuster, including the release mechanism if present, may be automated. For example, the volume adjuster may be moveable between an engaged and disengaged position by the press of a button and/or the release mechanism may be controllable by the press of a button.

Forming the Seal

As mentioned above, the seal assembly of the invention comprises a seal portion having a bladder comprising a shear thinning material.

FIG. 6 shows a process for manufacturing various seal portions comprising a shear thinning material. As shown in FIG. 6, the process begins with a seal portion comprising an empty bladder 105, that is, a bladder 105 without shear thinning material (FIG. 6A). The empty bladder 105 is unsealed and may be filled, for example injected, with various amounts of shear thinning material 101, for example to allow for a particular facial engagement volume as described in more detail below. FIGS. 6B to 6E show the bladder 105 substantially 100% filled, about 75% filled, about 50% filled and about 25% filled with shear thinning material 101 respectively. After filling, any gas, for example air may be evacuated from the bladder 105. The bladder 105 is then sealed, for example at the point of manufacture.

FIG. 6F shows a seal portion comprising a bladder 105 that is substantially 100% filled with shear thinning material 101. As a result, the bladder 105 of FIG. 6F is under tension.

Figure 6A:
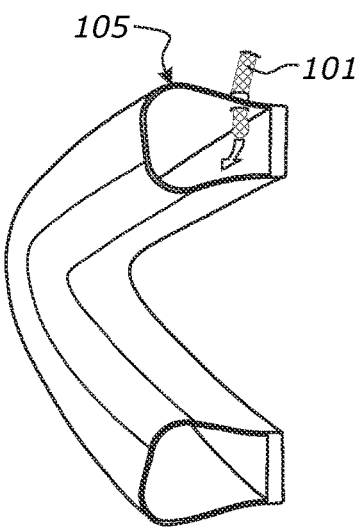
Figure 6B:
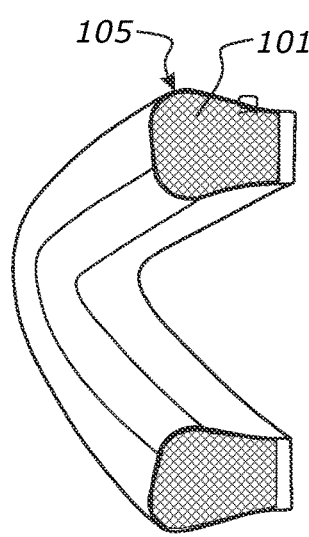
Figure 6C:
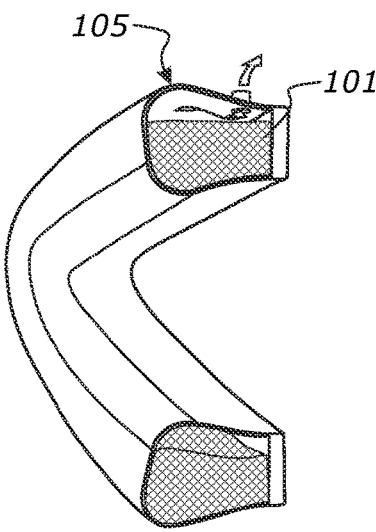
Figure 6D:
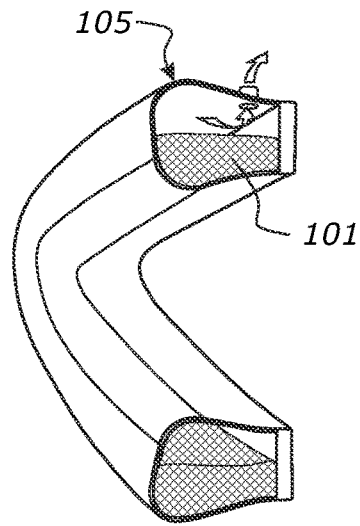
Figure 6E:
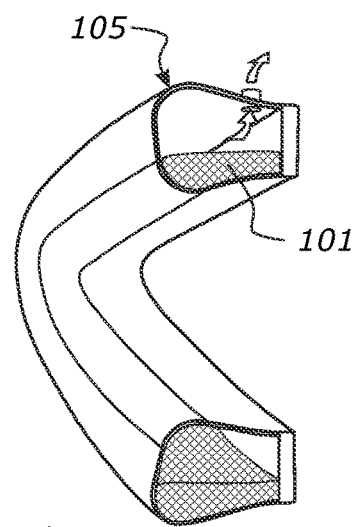

In contrast to FIG. 6F, FIGS. 6G to 6I show seal portions comprising bladders 105 that are partially filled with shear thinning material. In these embodiments, there is not enough shear thinning material 101 to put the wall 160 of the seal portion under tension. Therefore, after the evacuation of gas from the bladder 105, as shown in FIGS. 6C to 6E, the resulting seal portions may be in a collapsed state as shown in FIGS. 6G to 6I respectively. In the collapsed state the walls 160 may buckle, fold, gather or pleat. However, the length of the wall 160 of each seal portion from point A to B remains the same at rest (that is, when the seal is not fitted to a user) regardless of whether the wall 160 is under tension (FIG. 6F) or in a collapsed state (FIGS. 6G to 6I).

Fitting the Seal Assembly to a User

Figure 7A:
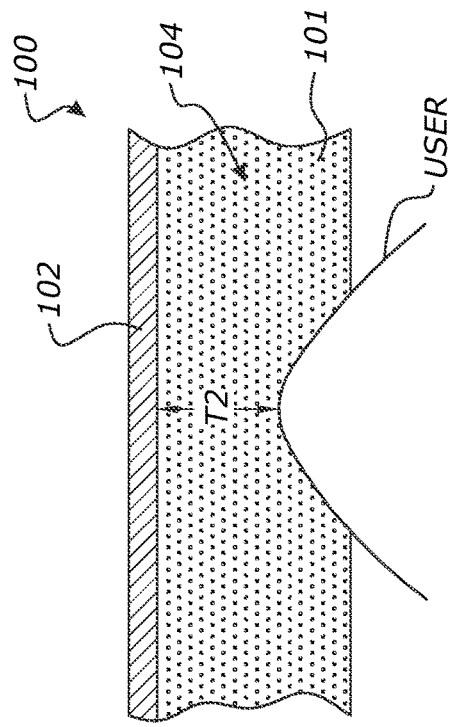
FIGS. 7A-7D are schematic cross-sectional views of a seal portion 104 of a seal assembly 100 in accordance with an embodiment of the invention, illustrating the process of adapting the seal portion 104 to the shape of a particular user's face and transitioning the shear thinning material 101 in the seal portion between a state of higher viscosity and a state of lower viscosity.
Figure 7B:
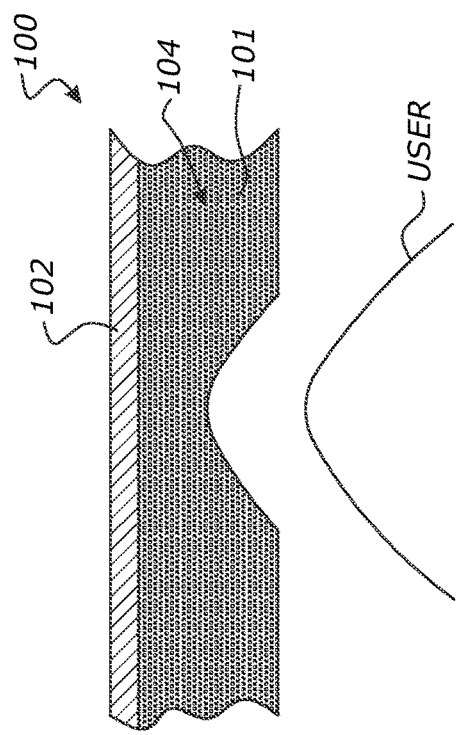
Figure 7C:
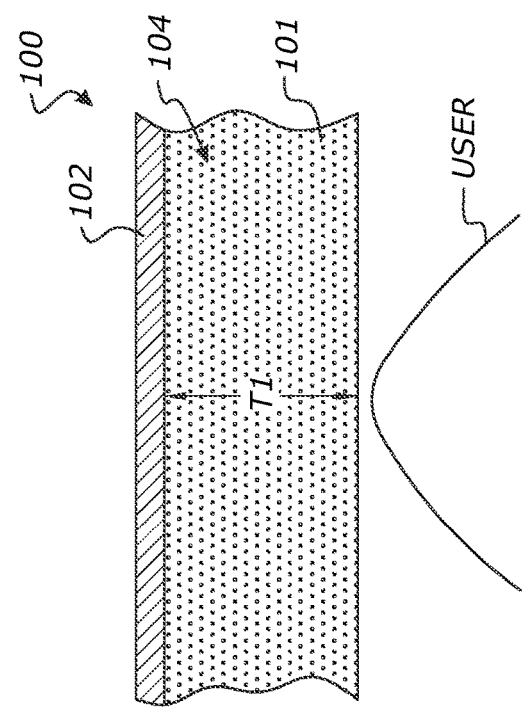
Figure 7D:
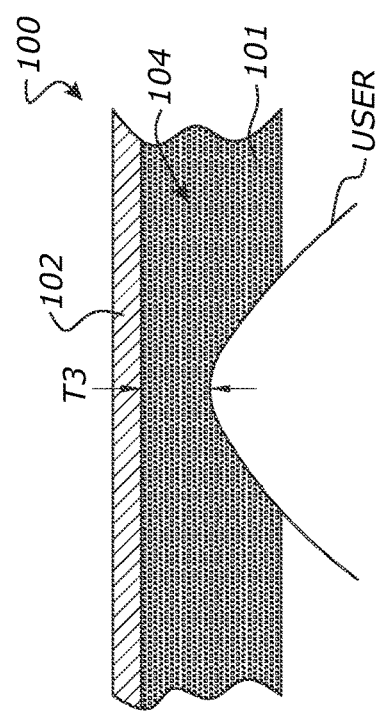

FIGS. 7A-7D illustrate the changes in the properties of the shear thinning material 101 within the seal portion 104, as the seal assembly 100 is donned by a user (FIGS. 7A-7C) and after the seal assembly 100 is removed from the user's face (FIG. 7D).

Firstly, FIG. 7A illustrates a generic seal assembly 100 of the invention comprising a seal portion 104 having a bladder with a capacity V3, the internal resting volume. As shown in FIG. 7A the seal portion may comprise a housing portion 102. A shear thinning material may be introduced into the bladder, for example by injection into the bladder as described above. The capacity of the bladder is given by equation 1:

$$V3 = V4 + V5 \qquad \text{Equation 1}$$

where V3 is the bladder capacity, V4 is the volume of shear thinning material and V5 is a predetermined facial engagement volume. During manufacture or in use, in some embodiments any gas present in the facial engagement volume may be evacuated such that the facial engagement volume is in a collapsed state as described above. In this state the shear thinning material may still be distributed within the bladder.

With reference to FIG. 7A, the bladder has a thickness T1 as shown in FIG. 7A resulting from the shear thinning material at least partially filling the internal resting volume V3. It should be understood that in some embodiments, depending on the nature of the bladder and the shear thinning material, the facial engagement volume V5 may be 0, or close to 0, such that V3 is substantially equal to V4. In other embodiments V5 may be greater than zero, as described above.

The shear thinning materials described herein behave as solids at rest. When a user's face is pressed against the seal portion of a seal assembly according to the invention, the shear thinning material continues to behave as a solid until the shear stress experienced by the shear thinning material exceeds the shear stress yield threshold of the material. At this point the shear thinning material starts to behave as a fluid and redistributes around the bladder, and into the facial engagement volume where present, conforming to the facial geometry of the user. This concept is shown in FIG. 7B which illustrates an interface 100 partially pressed against the geometry of a user's face. The user's facial volume is added to the predetermined facial engagement volume V5 of the bladder so that the seal portion 104 has a reduced thickness T2 and the shear thinning material redistributes through the volume V3.

FIG. 7C illustrates a state of seal assembly 100 after a user's facial geometry has been fully pressed into the seal portion 104, taking up the volume V5 of the seal portion 104 allocated to the predetermined facial geometry of the user. At this stage the thickness of the seal portion 104 is further reduced to a thickness of T3 and the equation V3=V4+V5 is satisfied. To achieve a tighter fit, the interface may be pushed further up against the user's face, including for example, by engaging one or more volume adjusters if present.

As explained above, engagement of the volume adjuster leads to a reduced internal volume of the seal portion/bladder, leading to further redistribution of the shear thinning material inside the bladder such that the walls of the bladder may swell and inflate.

In some embodiments the bladder may be adapted to expand to an internal volume greater than 100, 105, 110, 115, 120% or more of the internal resting volume of the bladder, and suitable ranges may be selected from any of these values, for example from about 100 to about 120%, or from about 100 to about 110%, or from about 100 to about 105% of the internal resting volume of the bladder.

In some embodiments when the internal volume of the bladder is greater than 100% of the internal resting volume, the seal portion may be deformed further against the facial geometry of the user. In some embodiments this may lead to a more even distribution of the load from an associated headgear across the sealing surface of a user's face and a tighter and more conformed seal.

After the shear stress is removed from the seal portion, for example if the user stops moving, the shear thinning material once again acts like a solid, maintaining its conformed shape against the facial geometry of the user. This is beneficial because at rest the seal portion retains no stored spring energy which is a common detrimental problem in compressed elastomeric seals. FIG. 7D illustrates this principle, showing the bladder of the seal portion 104 maintaining the deformed shape achieved as described above with reference to FIG. 7C, even after the seal assembly 100 is removed from a user's face.

Fitting the Seal Assemblies to a Range of Facial Geometries

Figure 8A:
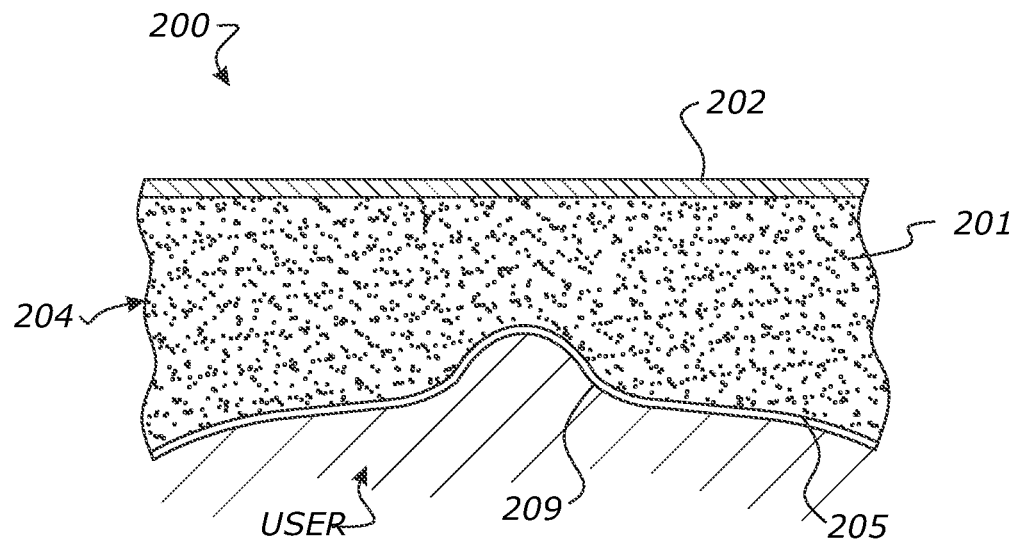
FIGS. 8A and 8B are schematic cross-sectional diagrams taken along line 5-5 of FIG. 4A, illustrating the application of the seal portion 204 of a seal assembly 200 according to an embodiment of the invention to the face of a user having a flatter face and a user with a larger nose bridge and a more deeply contoured face respectively.
Figure 8B:
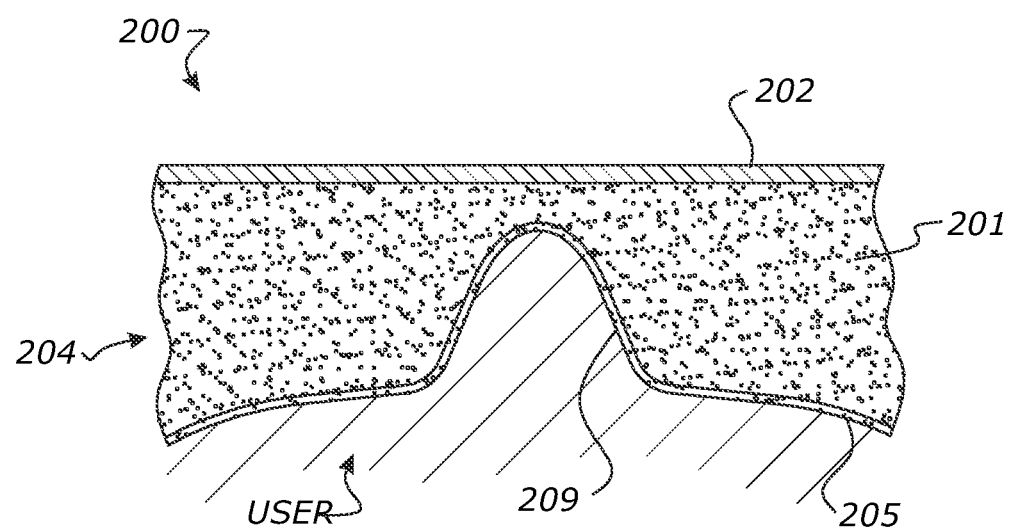

Shear thinning materials may be used in a number of seal assemblies described herein and can be used to aid the conformance of seals with faces of different shapes. FIGS. 8A and 8B use full face assembly 200 as an example to illustrate this concept. FIGS. 8A and 8B generally correspond to the cross-section identified by the line 5-5 in FIG. 4A, showing a partial cross section through an area of a seal portion 204 and housing portion 202 extending over a bridge of a user's nose and across and onto portions of the patient's cheek adjacent to the nose bridge. The cross-section of FIGS. 8A and 8B are intended to pass through the sealing surface 209 between the seal portion 204 and skin of the user's face.

As shown in FIGS. 8A and 8B, the seal portion 204 of the seal assembly 200 comprises a bladder 205 comprising a shear thinning material 201. FIG. 8A illustrates the application of the seal assembly 200 to a user having a flatter face with a shallower nose bridge. By contrast, FIG. 8B illustrates the application of seal assembly 200 to a patient having a much larger nose and more pointed face.

In various embodiments, to assist in conforming the seal assembly, the seal portion can be made of any flexible and/or elastic material such as, but not limited to, silicone rubber or thermoplastic elastomers, enabling it to conform readily to the facial geometry of a user. Forming the seal portion with a flexible elastic outer casing can help the shear thinning material within the seal portion achieve a tighter seal with the facial geometry of a user because the material forming the seal portion can expand to accommodate the user's facial engagement volume. This can provide the additional optional benefit of achieving and maintaining a conformed shape as described above. Additionally, the shear thinning material within the seal portion, or within the bladder within the seal portion can freely move and conform to a user's facial geometry when in a reduced viscosity or "fluid state".

Figure 9A:
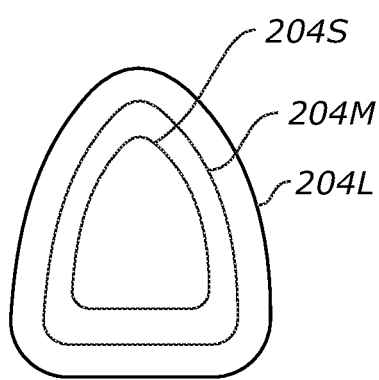
FIGS. 9A-9E illustrate various seal portions 204, 304, 404, 504 and 604 of seal assemblies according to embodiments of the invention, showing that the seal portion 204, 304, 404, 504 and 604 may be manufactured in different sizes, where S=small, M=medium and L=large.
Figure 9B:
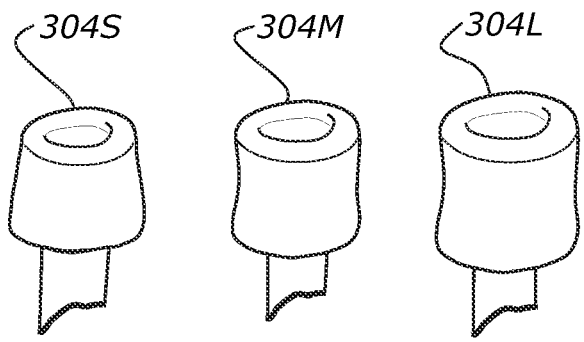
Figure 9C:
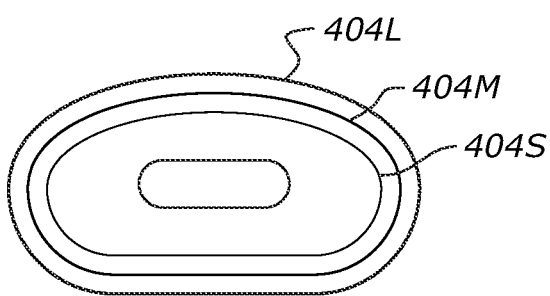
Figure 9D:
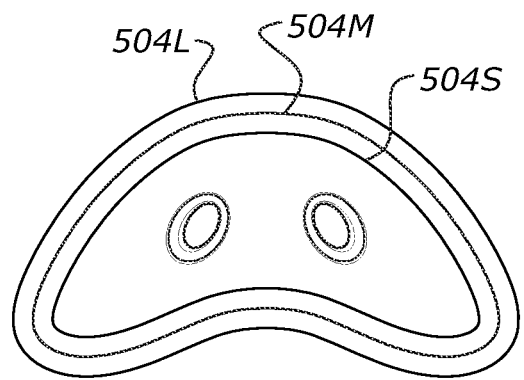
Figure 9E:
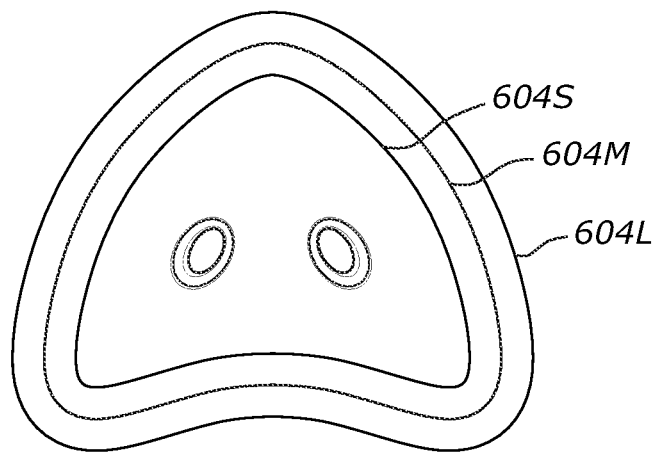

In embodiments where the bladder forms the seal portion. The seal portion can be made in a plurality of different sizes. The bladder may be formed from an elastic material. FIG. 9A shows a full face seal assembly 200 in which the seal portion 204 may be made of different sizes illustrated as 204L for the large size, 204M for the medium size, and 204S for the small size. This concept is also applicable to seal assembly types other than full-face seal assemblies 200, for example seal assemblies 300, 400, 500 and 600 shown in FIGS. 9B-9E respectively. In the case of nasal prong assemblies 300, nasal prongs with seal portions 304 of different sizes may be manufactured as shown in FIG. 9B. This type of seal assembly 300 is discussed in more detail further below.

In some embodiments a range of seal portions and/or housing portions may be made in different sizes to accommodate the wide-range of facial geometries present in the population. For example, FIGS. 10A-10D show an embodiment of the invention identified generally by the reference numeral 400 (corresponding to the around-the-mouth seal assembly also shown in FIG. 2C). FIGS. 10A-10E show an around the mouth seal assemblies with a sealing surface conforming to lips of larger (FIGS. 10A and 10B) and smaller (FIGS. 10C and 10D) radii.

With continued reference to FIGS. 10A-10D, in some embodiments users may be able to purchase a particular sized housing portion 402 and/or a particular sized seal portion 404 and combine the housing portion 402 and the seal portion 404 to provide the best fit in terms of the user's facial geometry. It will be apparent to a person skilled in the art that this concept is also applicable to the other seal assemblies described herein, including assemblies 200, 300, 500 and 600 shown in FIGS. 2A, 2B, 2D and 2E respectively.

Instead of providing housing portions and/or seal portions of different sizes, custom seal assemblies may be adapted to fit a particular user by providing a seal portion of a standard size and removing a facial engagement volume from the bladder of the seal portion that matches that user prior to sealing the bladder.

The ability to modify the size of the seal assembly of the invention can also be used to provide different sealing arrangements. For example, with reference to FIGS. 2A and 4A-4C, in full-face mask embodiments 200, where the seal portion 204 is configured to fit around a user's nose and mouth, it may be beneficial to be able to change the arrangement of the seal portion 204 to sit above or below the chin of the user. This can improve user comfort and compliance.

In some embodiments the seal assemblies of the invention may be made with a surface finish on the seal portion that provides sufficient friction between a user's skin to allow the seal portion to move with the user's skin as the user's facial geometry changes. The surface finish may comprise small protrusions, for example ribs on the surface of the seal portion.

Types of Seal Assemblies and Modifications

The ability to make modifications to the size of the seal portion can also provide for the use of the shear thinning materials in different types of seal assemblies as discussed above. For example the shear thinning materials described herein may be used in assemblies 200-600. Full-face masks, for example seal assembly 200, have already been described in detail above. The following is a description of some of the other types of seal assemblies contemplated herein as well as modifications that may be made to the seal assemblies and interfaces of the invention.

Nasal Assemblies

In some embodiments the seal assembly of the invention may be a nasal assembly 300, for example nasal assembly 300 depicted in FIG. 2B.

FIGS. 11-16 show an embodiment of the invention identified generally by the reference numeral 300 as shown in FIG. 2B. Parts, components and features of the interface 100 which are similar or the same as corresponding parts or features of the interface 100 are identified by the same reference numeral except that a value of 200 has been added thereto.

Figure 11A:
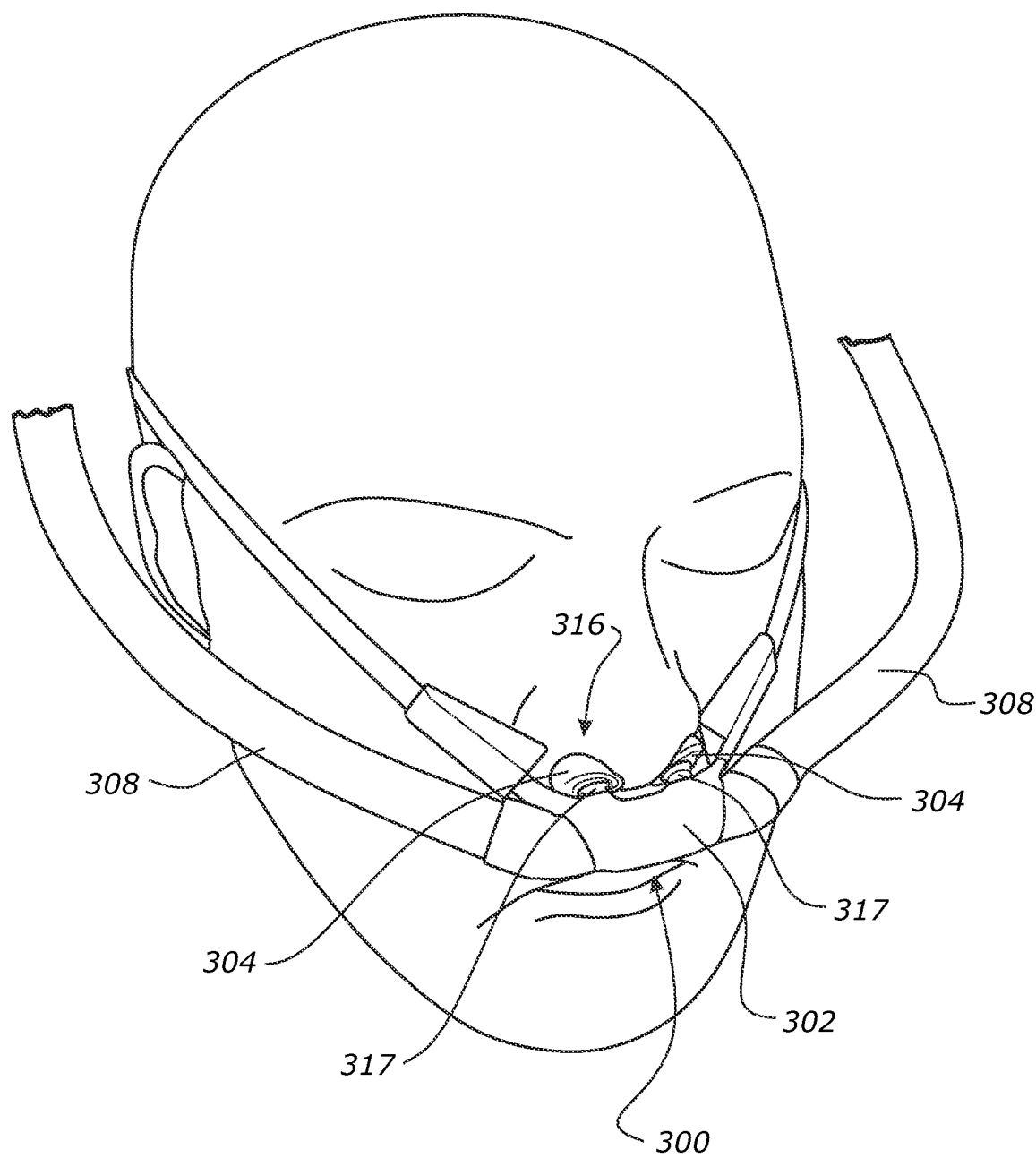
FIGS. 11A and 11B are perspective views of a respiratory interfaces comprising seal assembly 300, according to embodiments of the invention.
Figure 11B:
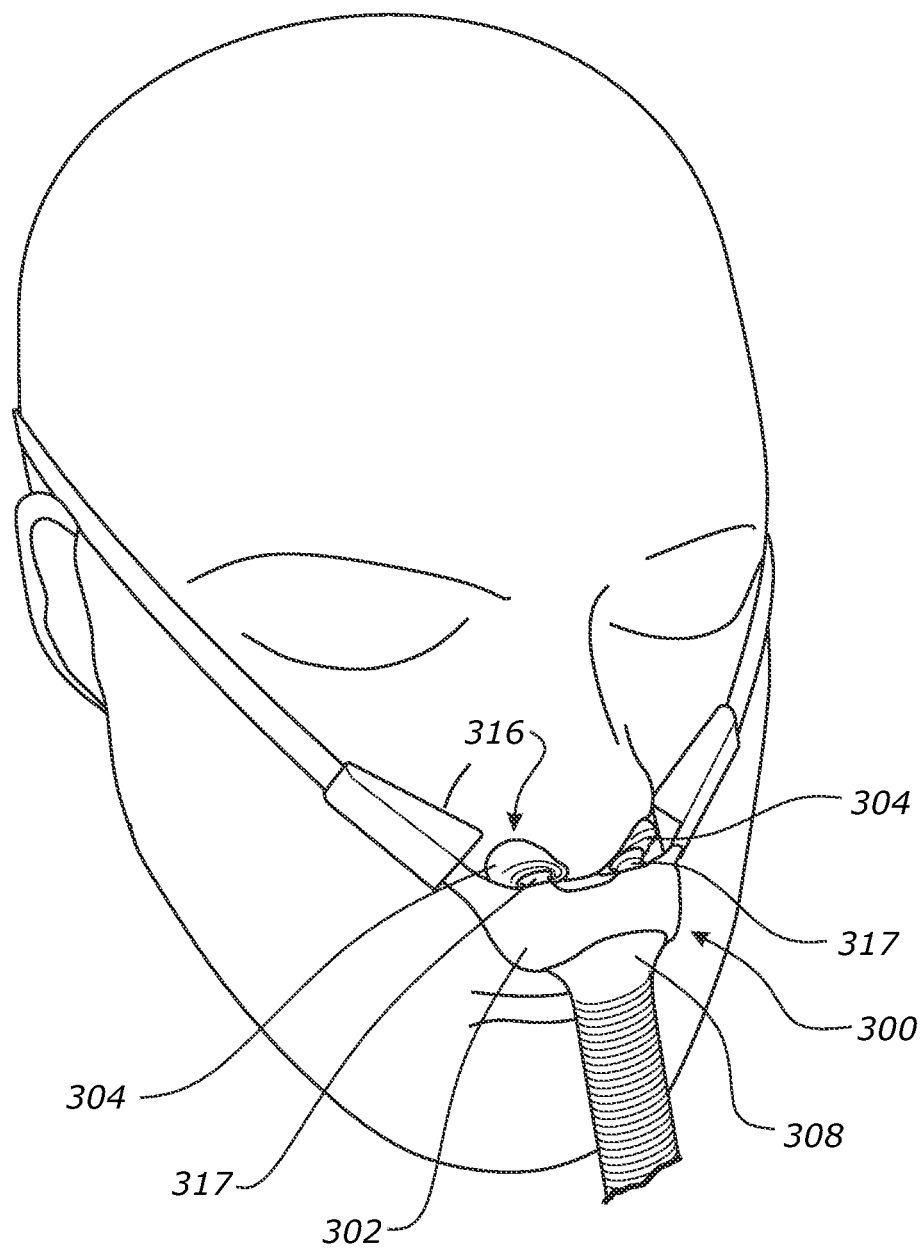

FIGS. 11A and 11B show interfaces comprising seal assembly 300, and associated headgear. In both FIGS. 11A and 11B, seal assembly 300 comprises two nasal prongs 316, each comprising a seal portion 304 and a nasal stem 317. In various embodiments the seal portion 304 of each nasal prong 316 may comprise a shear thinning material.

With continued reference to FIGS. 11A and 11B, the nasal prongs 316 comprise seal portions 304 that correspond to the seal portion 104 of interface 100. The nasal prongs 316 each comprise a flow path through the seal portions 304, for delivery of respiratory gas to the user. For example, in various embodiments the flow path may be a stem 317 extending from the frame and through the seal portion 304, each stem 317 defining the flow path to the user's nare. The flow path therefore allows fluid connection of the user's airway with a conduit 308 supplying a source of breathable gas to the user. The two nasal prongs 316 may be provided to a housing portion 302 by nasal stems 317. In some embodiments the nasal stems 317 may be permanently attached to or may be detachable from the housing portion 302.

FIGS. 11A and 11B differ from each other in the location of the orientation of the air conduit 308 relative to seal assembly 300. FIG. 11A illustrates the supply of breathable gas through a split air conduit 308 that loops around from the user's face to the back of the user's head where it connects with a gas/air supply (not shown). In contrast, FIG. 11B illustrates the supply of breathable gas through a single air conduit 308.

In one embodiment the nasal stems 317 of nasal seal assemblies 300 such as those shown in FIGS. 11A and 11B may be rotatable and flexible at the base where they connect to the housing portion 302. For example, each nasal stem 317 may be made from any polymeric material have sufficient rigidity, such as a plastic or an elastomer, including silicone and may further comprise one or more thinned regions at its base.

With continued reference to FIGS. 11A and 11B, the seal portion 304 of each nasal prong 316 may have an angular tip such that the seal portions 304 are better adapted to deform to the shape of the nares of a user.

Figure 10A:
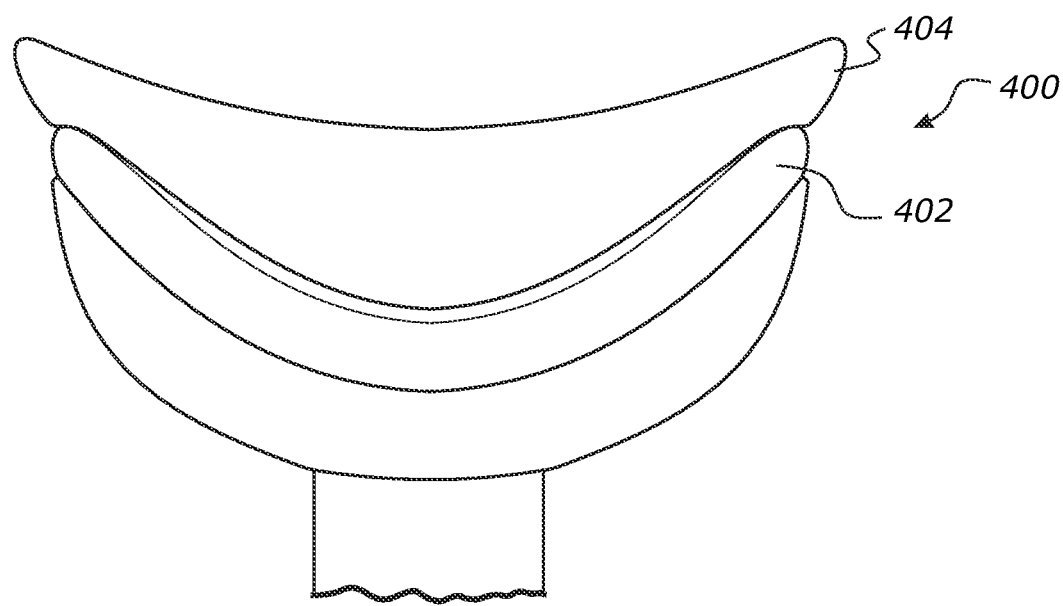
FIGS. 10A-10D are schematic views showing seal assemblies 400 comprising housing portions 402 and seal portions 404 of different radii in accordance with embodiments of the invention.
Figure 10B:
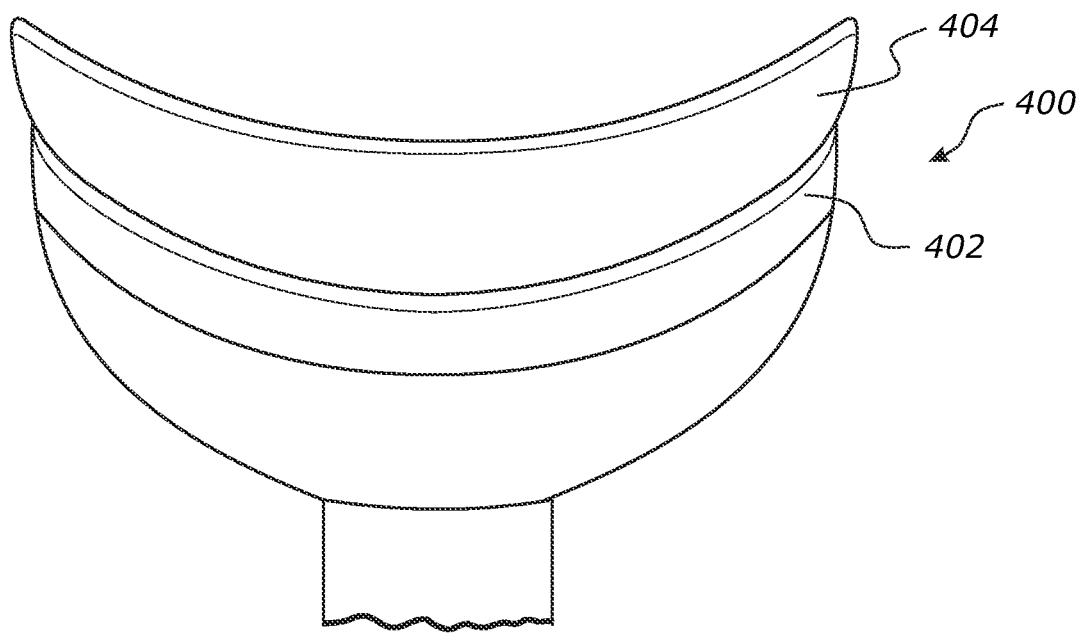
Figure 10C:
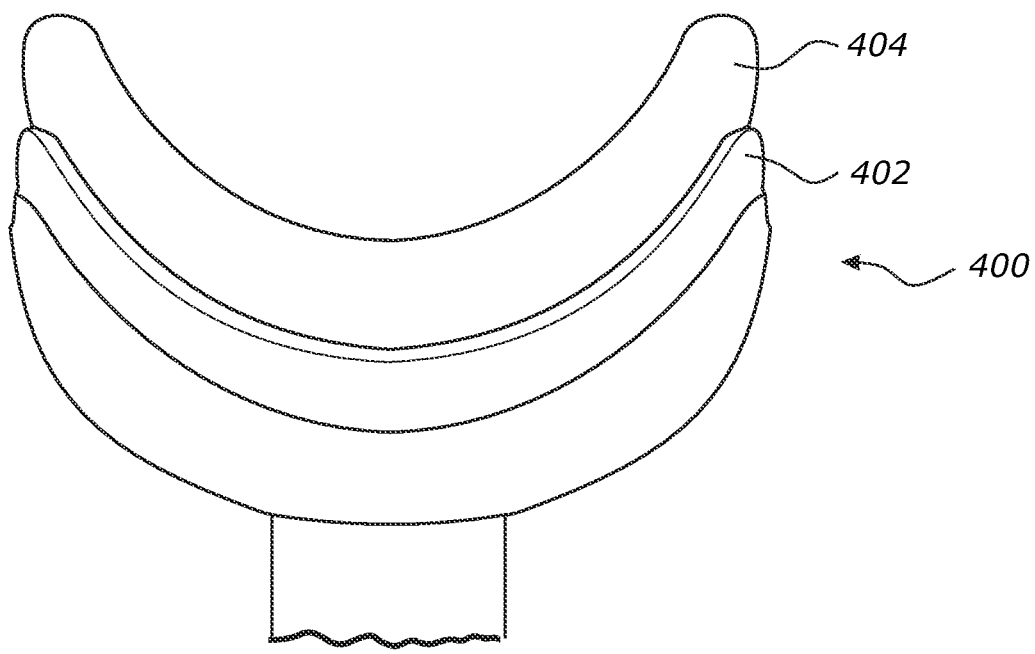
Figure 10D:
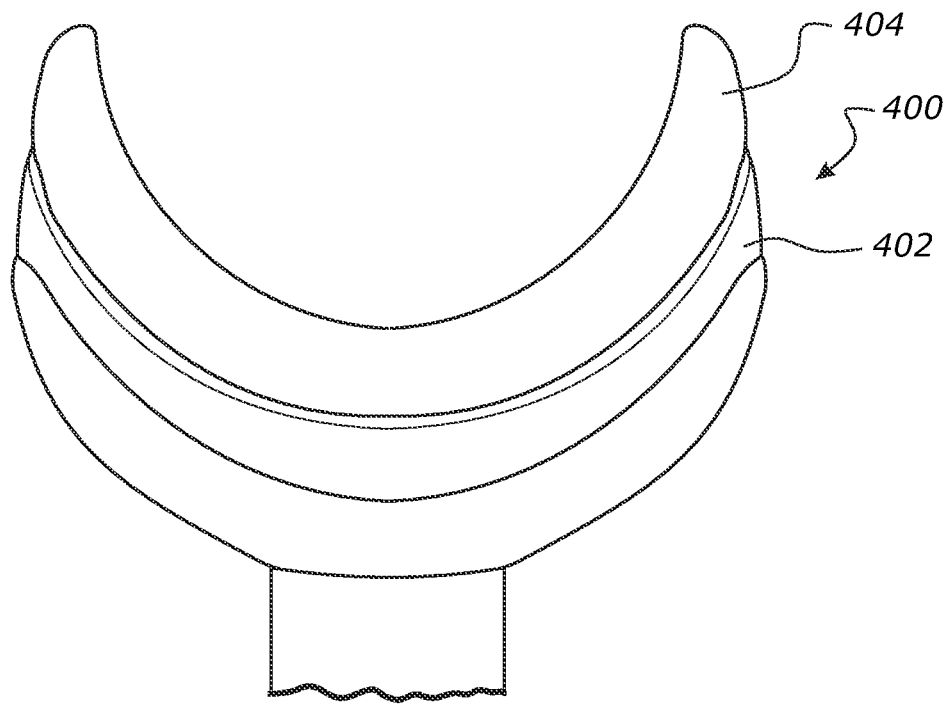

The nasal assemblies 300 shown in FIGS. 11A and 10B may behave in a similar manner to cannula-type interfaces, allowing the nasal stems 317 to enter the nasal passages of a user.

The method of fitting nasal assemblies 300 such as those shown in FIGS. 11A and 11B to the facial geometry of a user are the same as those described above with reference to interface 100, the difference being that the sealing surface corresponds to all or part of the seal portion 304 of each nasal prong 316 depending on whether the nasal prongs 316 adopt a tight-fit or loose-fit. This is discussed in more detail below.

With reference to FIGS. 11A and 11B, as the nasal assembly 300 is inserted into the nasal cavity, the shear thinning material in the seal portion 304 of the nasal prong 316 redistributes and cushions against the inside of the user's nose until the capacity of the seal portion 304 reaches 100%. Referring to equation 1 above, this occurs when the user's nostrils take up the volume V5 of the seal portion 304 allocated to the predetermined facial engagement volume of the user. In this embodiment, the inside of the nostrils and the entrance of the nares represent the parts of the face that contact the sealing surface of the seal portion 304.

With continued reference to FIGS. 11A and 11B, in various embodiments the seal portion 304 of each nasal prong 316 may comprise a bladder, for example a resilient bladder (not shown), comprising one or more shear thinning materials. As described above, the bladder has an internal volume which is the sum of the volume of shear thinning material and a predetermined facial engagement volume. The bladder may be a continuous chamber in the seal portion 304 of each nasal prong 316.

In the seal portion 304 of each nasal prong 316 or the bladder if present, the shear thinning material may form at least about 60, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.9, or 100% of the seal portion 304 of each nasal prong 316 or bladder at rest (internal resting volume) and useful ranges may be selected from any of these values, for example from about 65 to about 70, about 65 to about 75, from about 65 to about 80, from about 60 to about 85, from about 65 to about 90, from about 65 to about 95, from about 70 to about 80, or from about 70 to about 85%, from about 70 to about 90, from about 70 to about 95, from about 75 to about 80, from about 75 to about 85, from about 75 to about 90, from about 75 to about 95, from about 80 to about 90, from about 80 to about 95, or from about 60 to about 100%.

Other aspects described under the heading 'location and nature of shear thinning material' above are also applicable to the interface 300, for example, the presence of multiple compartments or multiple bladders within the seal portion of each nasal prong.

Figure 12A:
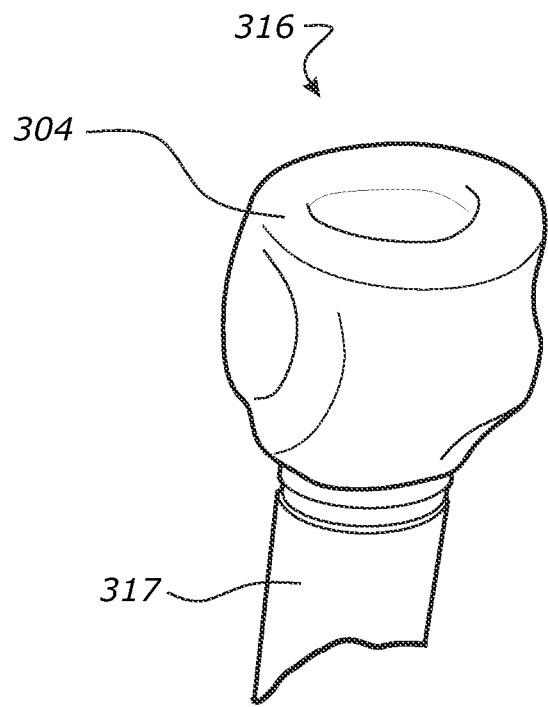
FIGS. 12A and 12B are perspective views of a nasal prong 316 of a seal assembly in accordance with an embodiment of the invention, showing the shape that the seal portion 304 of the nasal prong 316 may adopt before (FIG. 12A) and after (FIG. 12B) sealing with a user's nare.
Figure 12B:
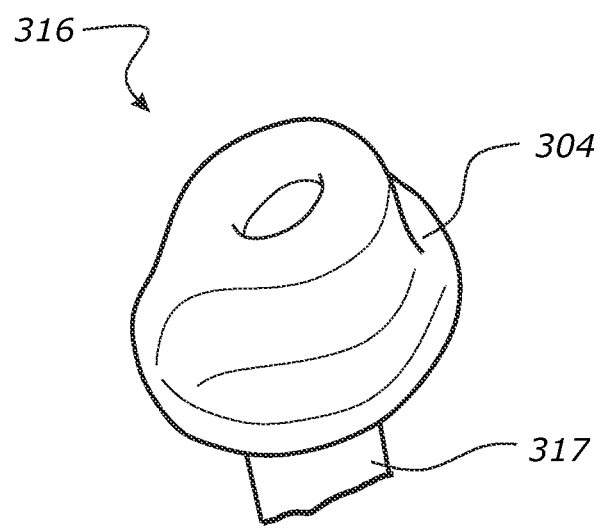

FIGS. 12A and 12B show the appearance of a seal portion 304 of nasal prong 316 before use (FIG. 12A) and after use (FIG. 12B) once the shear thinning material inside seal portion 304 or inside the bladder of the nasal prong 316 has redistributed around the shape of the nares of a user. FIG. 12B shows that the seal portion 304 maintains its deformed shape after it is removed from a user's nares. This allows the seal portion 304 to be fitted to a user more easily the next time that the seal assembly 300 is donned.

Each user will have their own preference as to the tightness of the seal assembly on their face. The tightness of the seal assembly will be determined at least partly by the force exerted on the user by the headgear associated with the seal assembly in a respiratory interface. The tightness preferences if different users can be accommodated by loosening or tightening the headgear associated with the seal assembly of a respiratory interface.

Figure 13A:
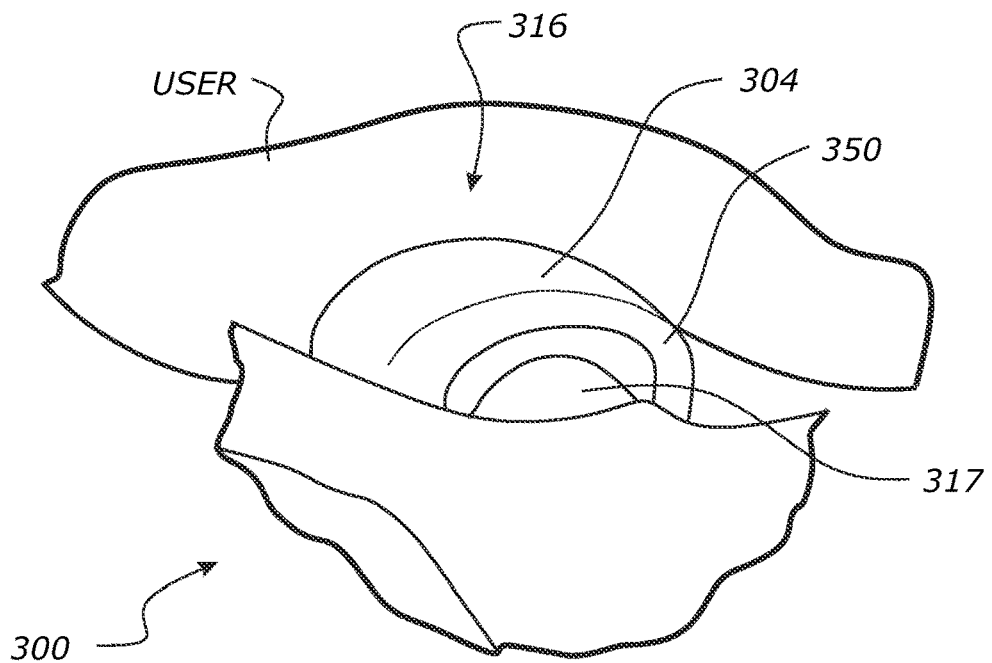
FIGS. 13A and 13B show a tight-fit (FIG. 13A) and a loose-fit (FIG. 13B) of the seal portion 304 of a seal assembly 300 according to an embodiment of the invention.
Figure 13B:
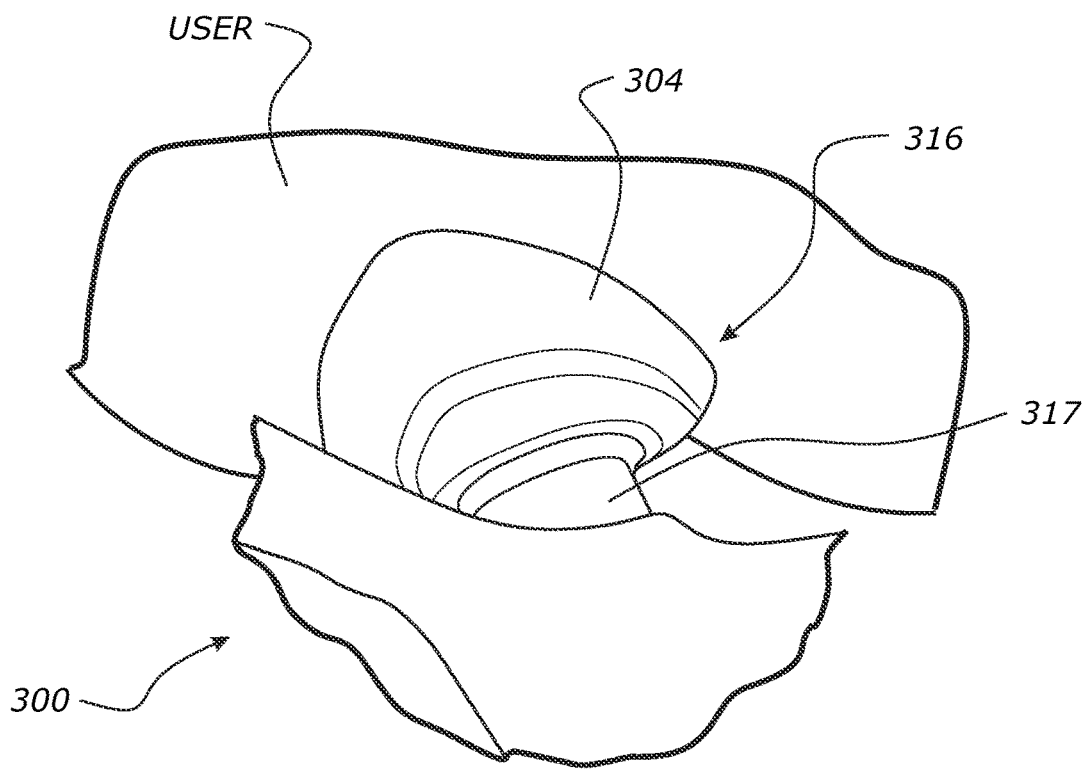

Seal assemblies of the invention have the ability to achieve an effective seal regardless of the level of force applied by a corresponding headgear, the tightness of which is set to a preferred level by a user. FIGS. 13A and 13B illustrate this concept using seal assembly 300 as an example, showing assembly 300 in tight fit and a loose-fit configurations respectively.

As shown in FIGS. 13A and 13B, the tightness of the fit of a seal assembly 300 will affect the shape of the seal portion 304 of the nasal prong 316 sealing with a user's nares. A tight fit may result in a rolling action of the seal on the underside of the seal portion 304 as the material in the seal portion 304 of the nasal prong 316 redistributes within the prong 316 to accommodate the facial geometry of the user. FIGS. 13A and 13B show contour lines that demonstrate the difference in the shape of the seal portion 304 in a tight-fit configuration and a loose-fit configuration respectively. FIG. 13A shows the rolling edge 350 of seal portion 304 that may result with a tight-fitting seal assembly 300, resulting from headgear that is set to a tight fit by the user.

In some embodiments a user may prefer a tight fitting nasal prong 316 or a loose fitting nasal prong 316, for example as shown in FIGS. 13A and 13B respectively.

In both tight fit and loose fit configurations, the seal portion of the seal assembly is able to form an effective seal with the face of a user, despite the variance in the tensile force that may be applied by a headgear used with a particular respiratory interface. The inventors believe that this is a unique advantage of the presently described seal assemblies. The seal portions of other described herein, for example seal assemblies 200, 400, 500 and 600 are also able to achieve a tight-fit and loose-fit.

In some embodiments the nasal prongs 316 may be made by moulding, for example by moulding over a solid core mould such as the mould 320 shown in FIGS. 14A-14D. In various embodiments the mould 320 may extend all the way though nasal prong 316 including though the seal portion 304 and the nasal stem 317 as is shown in FIG. 14C. This results in a hollow nasal prong 316, that is, a nasal prong 316 with an internal hollow (stem) tube, which acts as a flow path through the seal portion 304 to allow fluid communication of a user's airways with a source of breathable gas, for delivery of respiratory gas to the user.

With continued reference to FIGS. 14A-14D, to prepare nasal prongs 316, a first material and a second material for forming the nasal stem 317 and the seal portion 304 are selected respectively. In some embodiments the first material is coated along the stem 321 of mould 320, to form the nasal stem 317 of nasal prong 316. In some embodiments a second material is used to coat the bulb 322 of the mould, to form the prong head 323 which will come to form the seal portion 304 of the nasal prong 316, as is shown in FIG. 14D. After coating the first and second materials, the first and second materials are allowed to set along the length of the mould 320. The materials may be set by any means known in the art, for example the materials may be molten and may be set by cooling.

In some embodiments the nasal stem 317 may be formed before the prong head 323. In some embodiments the prong head 323 may be formed before the nasal stem 317. In some embodiment the nasal stem 317 and the prong head 323 may be formed at the same time by coating and setting the first and second materials on the mould 320 substantially simultaneously.

In some embodiments the first and second materials for forming the nasal stem 317 and the prong head 323 may be the same. For example, it will be understood by a person skilled in the art that the nasal stem 317 may be made using the same material as prong head 323, albeit nasal stem 317 may comprise more than one layer of that material. This layering (or thickness) of the material may result in a more rigid structure of the nasal stem 317 as compared to prong head 323.

In various embodiments the first and second materials for forming the nasal stem 317 and the prong head 323, which will come to form the seal portion 304, may be different.

With continued reference to FIGS. 14A-14D, the second material (the material for forming the seal portion) may, for example, be any flexible and/or elastic material such as, but not limited to, silicone rubber or thermoplastic elastomer. In some embodiments the use of such flexible and/or elastic materials may encourage the de-moulding of the prong head 323 from the bulb 322 of mould 320 after the material sets, as is shown in FIG. 14B.

Furthermore, in some embodiments, preparing the nasal prongs 316 by over-moulding as described in the manner above may encourage the rolling behaviour that occurs when the nasal stem 317 is inserted deeper into a user's nostrils to achieve a tight-fit, for example as is shown in FIG. 13A.

As shown in FIG. 14B, to de-mould the prong head 323 from the mould, the prong head 323 may be rolled or folded back on to itself.

With reference to FIGS. 14A and 14B, the region where the first and second materials overlap (the over-moulding region) may comprise features, for example locking features such as ribs, that will come to assist in retaining the prong head 323 against the nasal stem 317 once the prong head 323 is rolled or folded off the mould.

With reference to FIG. 14C, after de-moulding the mould is extracted from the set nasal prong 316. The prong head 323 is then filled with a shear thinning material, such as for example, a shear thinning material having a shear thinning index useful herein, such as may be determined according to ASTM E3070-16. After filling, the prong head 323 is then sealed by any conventional means known to a person skilled in the art, thereby forming the seal portion 304 of nasal prong 316 as shown in FIG. 14D. In some embodiments the prong head 323 may be sealed to form the seal portion 304, and may be filled with shear thinning material after sealing, for example by injection as described previously.

In various embodiments, nasal prongs 316 of nasal assemblies 300, for example nasal prongs 316 formed by the method described above, comprise a hollow nasal stem 317 as shown in FIG. 14D. The hollow nature of nasal stem 316 provides a flow path through the seal portion and allows for a source of breathable gas to flow from an air conduit to a user.

In some embodiments nasal prongs 316 may be prepared by a method other than over-moulding. In some embodiments the flow path, for example hollow internal stem tube, required for supplying a source of breathable gas to a patient may be formed after preparation of the nasal prongs 316, for example by piercing each nasal prong 316 along its length.

Nasal prongs formed by the method of over-moulding described above, or by other methods may be attached to the housing portion of a seal assembly by any method known in the art, including for example gluing, interference fit, tapered fit, threading, over-moulding, welding, by the use of a circlip or any suitable chemical bonding process. In some embodiments the nasal stems of the nasal prongs may be permanently attached to or may be detachable from the housing portion of a seal assembly.

In some embodiments nasal prong assemblies 300, such as those shown in FIGS. 11A and 11B, may comprise a volume adjuster as described for interface 100. Such a volume adjuster may comprise, for example a pair of insertable members, for example a pair of pistons similar to those shown in FIGS. 5A and 5B for seal assembly 100.

In the case of nasal seal assemblies 300, and with reference to FIG. 14D, the volume adjuster may be located, for example at the attachment portion of the nasal prong 316, that is, where the seal portion 304 of nasal prong 316 attaches to the nasal stem 317.

In various embodiments of different seal assemblies and interfaces described herein, the shear thinning material within the seal portion may be able to redistribute around the facial geometry of the user and to accommodate movement of the user, without compromising the seal formed with the target treatment area R, for example one or more respiratory orifices of a patient.

FIGS. 15A-15C use nasal assembly 300 as an example to illustrate the concept that seal assemblies and interfaces of the invention are capable of accommodating a range of angular adjustments. FIGS. 15B and 15C show the seal assembly 300 being tilted in the direction indicated by arrow A and then B respectively. In each case the shear thinning material within the seal portion 304 of the nasal prong 316 is able to redistribute within the seal portion 304 as required to maintain an effective seal.

FIGS. 16A-16C illustrate the seal assembly 300 being tilted in the direction indicated by arrows C or D, which correspond to different approach angles of the nasal prong 316. In each case, the shear thinning material is able to redistribute around the seal portion 304 of the prong 316 as required to maintain an effective seal.

Oral Seal Assemblies

In some embodiments the seal assembly of the invention may be an oral seal assembly 400, adapted to seal around the mouth of a user, for example to deliver a flow of breathable gas to the user.

FIGS. 17 and 18 show embodiments of the invention identified generally by the reference numeral 400. Parts, components and features of the interface 100 which are similar or the same as corresponding parts or features of the interface 100 are identified by the same reference numeral except that a value of 300 has been added thereto.

Figure 17C:
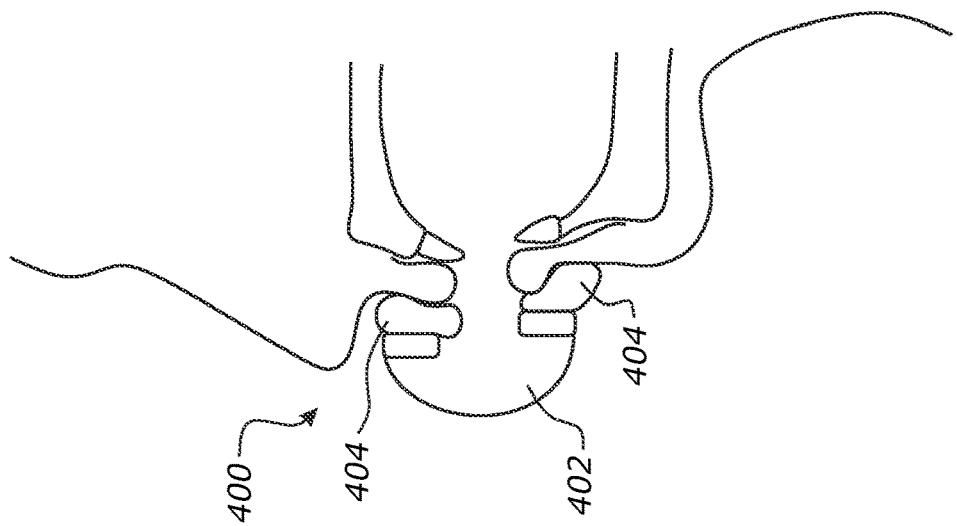
FIGS. 17A-17C are schematic views of a seal assembly 400 according to one embodiment of the invention, showing the ability of the shear thinning material to redistribute in the seal portion 404 as the facial geometry of the user changes from mouth closed (FIG. 17A) to mouth open (FIGS. 17B and 17C).
Figure 17B:
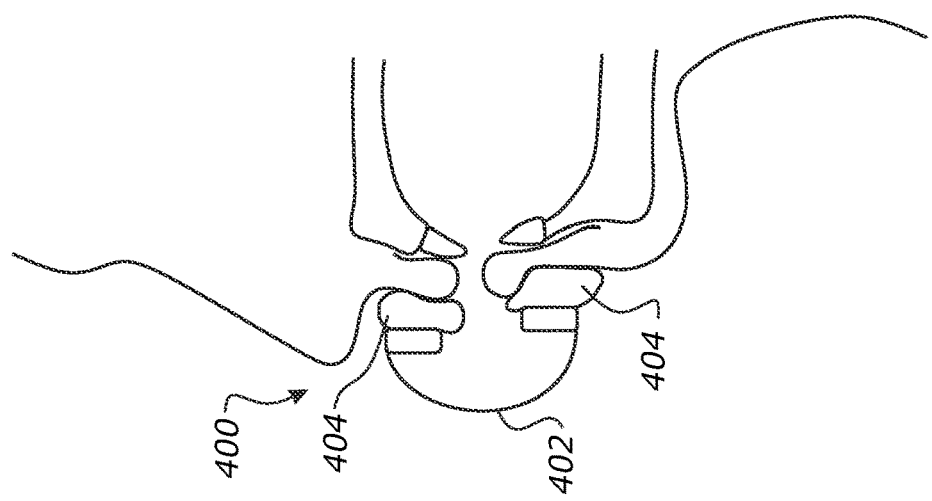
Figure 17A:
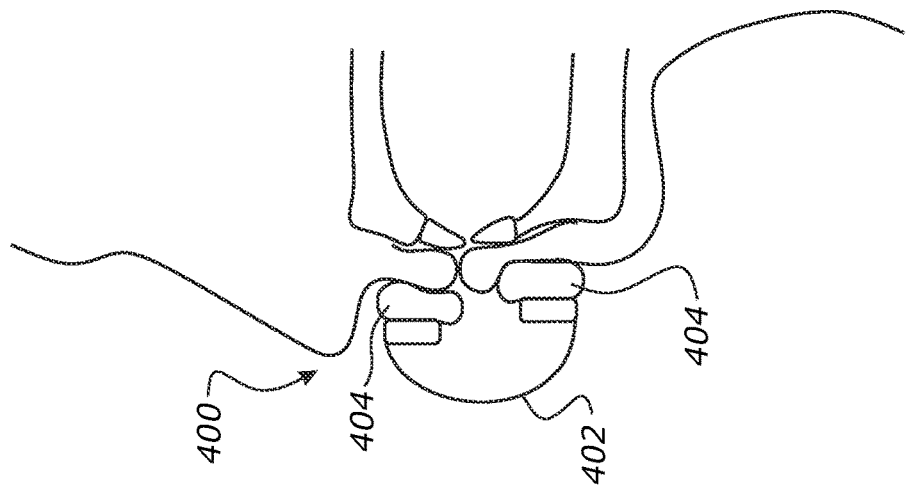

FIGS. 17A-17C show the oral seal assembly 400 also shown in FIGS. 10A-10E comprising a housing portion 402 and a seal portion 404 comprising a shear thinning material (not shown). FIG. 17A shows the position of the seal portion 404 when the user's mouth is closed and subsequent FIGS. 17B and 17C show how the seal portion 404 may change in shape as the shear thinning material redistributes in the seal portion 404 to accommodate the facial geometry of the user as the user's mouth opens. As described above, seal assembly 400 maintains an effective seal during this process.

Figure 18A:
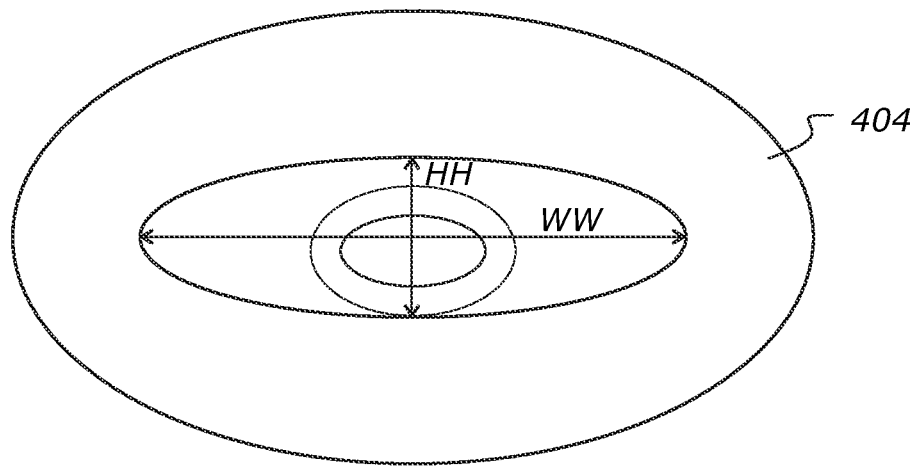
FIGS. 18A and 18B are schematic views of the seal portion 404 of a seal assembly according to one embodiment of the invention showing the change in the width WW and height HH of the flow path through the seal portion 404 for delivery of a respiratory gas to a user, as the mouth of the user adopts a closed (FIG. 18A) and open (FIG. 18B) position.
Figure 18B:
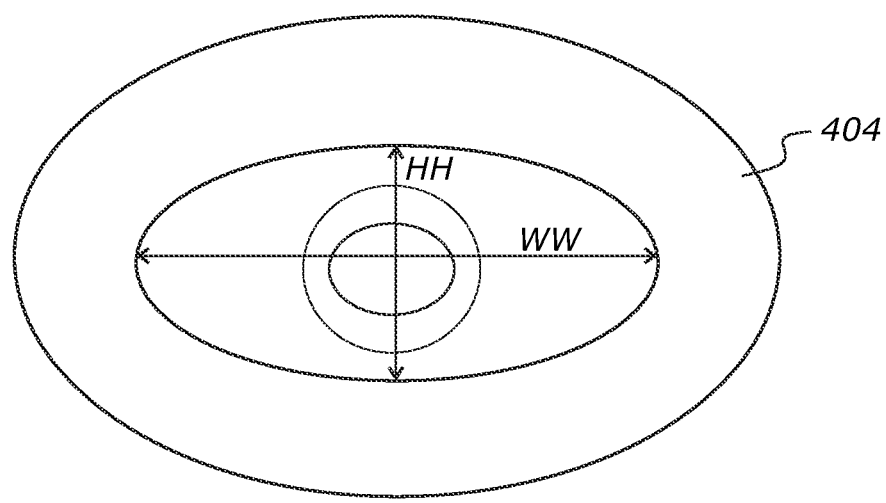

FIGS. 18A and 18B show another view of the interface 400 of FIGS. 17A and 17C, in particular illustrating the change in the width WW and height HH of the flow path through the seal portion 404 as the mouth of a user is closed (FIG. 18A) and opened (FIG. 18B).

In various embodiments, seal assembly 400, for example as shown in FIGS. 17A to 17C, may comprise a volume adjuster as described for interface 100. For example, the volume adjuster may comprise one or more insertable members, for example a pair of insertable members, such as a pair of pistons adapted to reciprocate within the housing 402 of seal assembly 400, to control the internal volume of a bladder as described above with reference to seal assembly 100. In some embodiments the volume adjuster in seal assembly 400 may be similar to that shown in FIGS. 5A and 5B.

With continued reference to FIGS. 17A to 17C, in one embodiment the seal portion 404 of an oral seal assembly 400 may comprise a bladder, comprising one or more shear thinning materials. As described above for other seal assemblies, the bladder of seal assembly 400 has an internal volume which is the sum of the volume of shear thinning material and a predetermined facial engagement volume. As for other embodiments, the bladder of a seal assembly 400, for example as shown in FIGS. 17A to 17C, may be a continuous chamber in the seal portion 404.

In the seal portion 404 or the resilient bladder if present of oral assembly 400, the shear thinning material may form at least about 60, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.9, or 100% of the seal portion 404 or the bladder at rest (resting internal volume) and useful ranges may be selected from any of these values, for example from about 65 to about 70, about 65 to about 75, from about 65 to about 80, from about 60 to about 85, from about 65 to about 90, from about 65 to about 95, from about 70 to about 80, or from about 70 to about 85%, from about 70 to about 90, from about 70 to about 95, from about 75 to about 80, from about 75 to about 85, from about 75 to about 90, from about 75 to about 95, from about 80 to about 90, from about 80 to about 95, or from about 60 to about 100%.

Nasal Interfaces

In some embodiments the seal assembly of the invention may be a nasal assembly 500 or 600 as shown in FIGS. 2D and 2E respectively.

FIGS. 19 and 20 also show embodiments of the invention identified generally by the reference numeral 500. Seal assembly 500 is also shown FIG. 2D. Parts, components and features of the seal assembly 100 which are similar or the same as corresponding parts or features of the seal assembly 100 are identified by the same reference numeral except that a value of 400 has been added thereto.

Figure 19A:
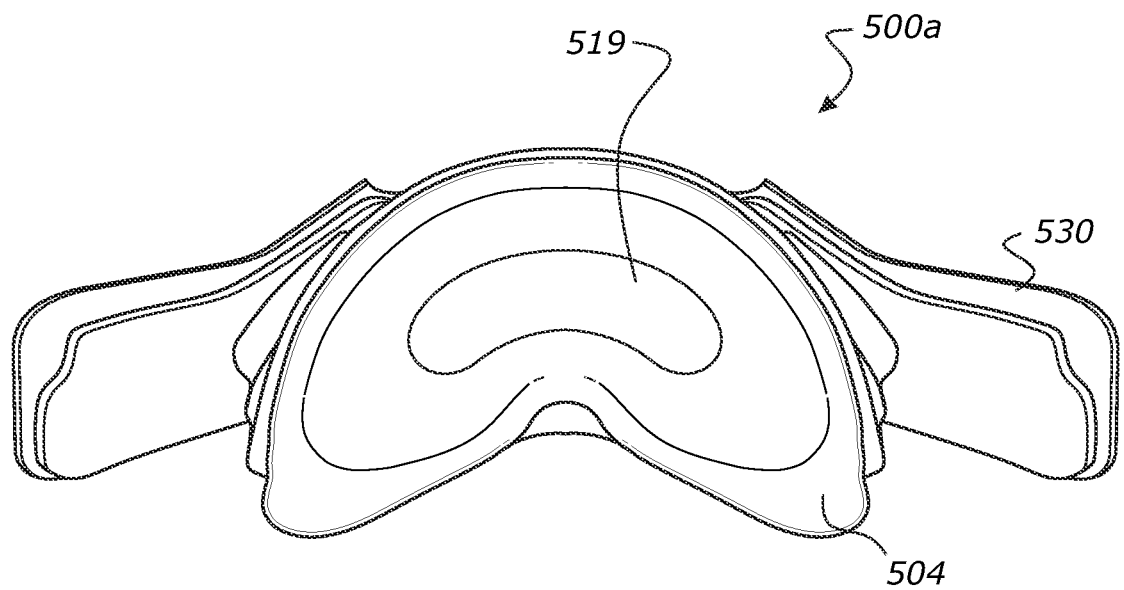
FIGS. 19A and 19B show perspective views of embodiments of the invention.

With reference to FIG. 19A in one embodiment seal assembly 500a comprises a flow path 519 through the seal portion 504 for fluid connection of the user's airway with a conduit for delivery of respiratory gas to the user. In one embodiment, seal assembly 500 may comprise two flow paths, for example two nasal apertures 519 (optionally comprising rigid internal stem tubes or cannulas 520) which are orifices that connect an air conduit with the airways of a user. This embodiment is denoted by the reference numeral 500b as is shown in FIG. 19B.

Figure 19B:
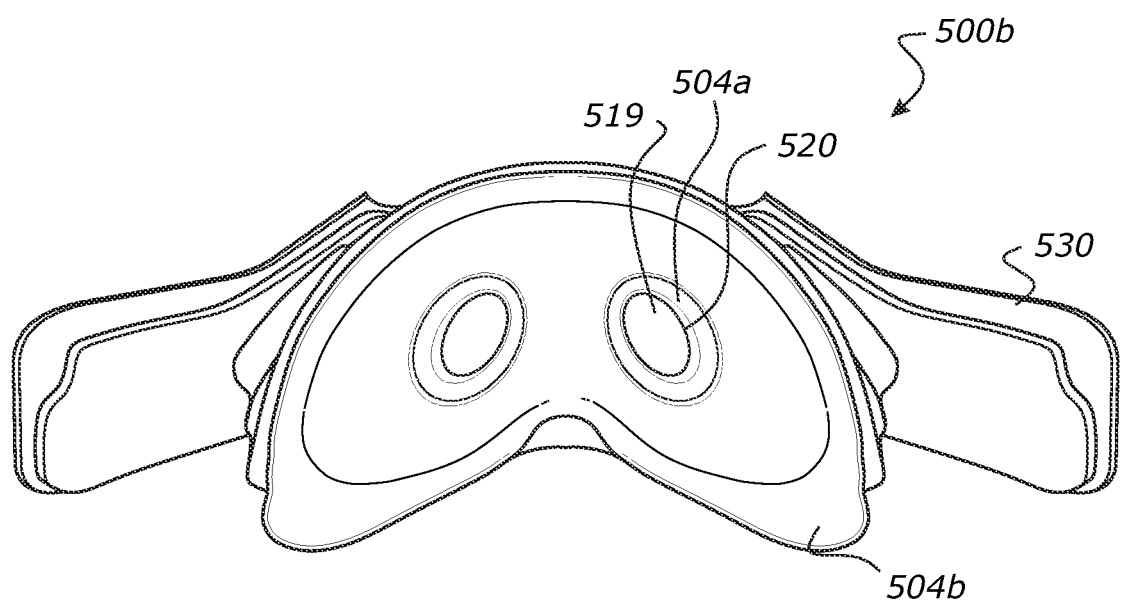

With continued reference to FIGS. 19A and 19B, the seal portion 504 in both interface 500a and 500b respectively, comprises one or more shear thinning materials as described herein. Due to the flow paths 519 directing breathable gas into the nostrils of a user, only a small portion of the seal portion 504a surrounding the nostrils may seal with the nares of the user in embodiment 500b shown in FIG. 19B. Alternatively, depending on the user's facial geometry, the seal portion 504 may interact with and seal against the facial geometry of the user at a number of locations, for example around the nares of the user (504a) and parts of the face of the user (504b) (see FIG. 19B).

Figure 20A:
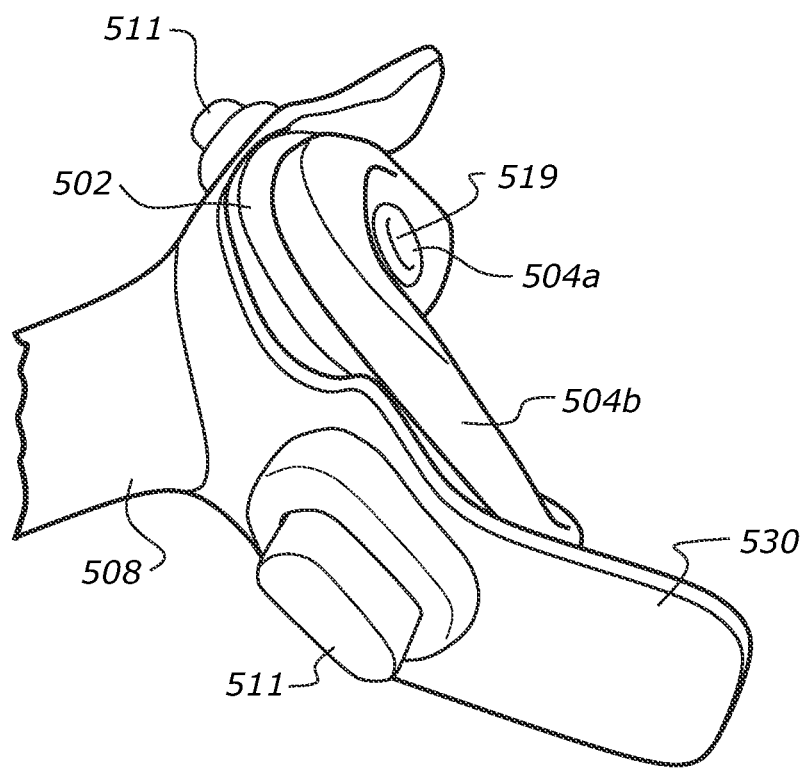
FIGS. 20A and 20B are perspective views showing the volume adjuster 511 in the embodiment of the invention illustrated in FIG. 19B.
Figure 20B:
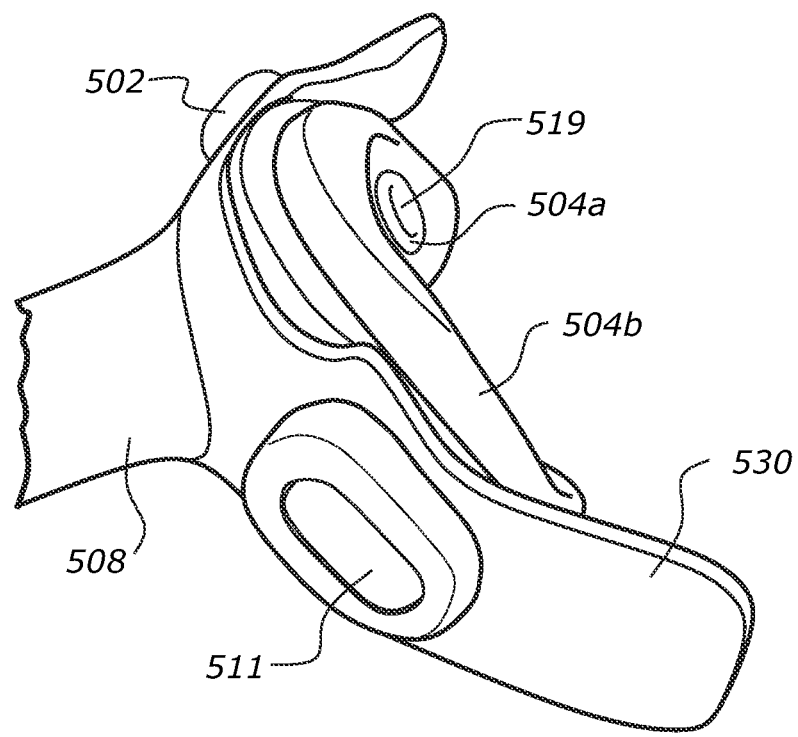

In some embodiments seal assembly 500 may comprise a volume adjuster as described herein. For example, the volume adjuster may comprise a pair of insertable members, such as a pair of pistons 511 as is shown in FIGS. 20A and 20B. The pistons 511 of FIGS. 20A and 20B may operate in the same way as the pistons described herein for other seal assemblies of the invention, for example those shown in FIGS. 5A and 5B.

In a modification of seal assembly 500, the seal assembly may extend over the top of the nasal bridge. This embodiment corresponds to seal assembly 600 as shown in FIG. 2E.

In some embodiments the seal portion of nasal seal assemblies 500 and/or 600 as shown in FIGS. 2D and 2E respectively, may comprises a bladder, comprising one or more shear thinning materials. As described above for other seal assemblies of the invention, the bladder has an internal volume which is the sum of the volume of shear thinning material within it and a predetermined facial engagement volume of a user. In some embodiments the bladder may be a continuous chamber in the seal portion.

With continued reference to seal assemblies 500 and 600 as shown in FIGS. 2D and 2E respectively, the shear thinning material may form at least about 60, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, 99.9, or 100% of the seal portion or the bladder of the seal portion at rest (resting internal volume) and useful ranges may be selected from any of these values, for example from about 65 to about 70, about 65 to about 75, from about 65 to about 80, from about 60 to about 85, from about 65 to about 90, from about 65 to about 95, from about 70 to about 80, or from about 70 to about 85%, from about 70 to about 90, from about 70 to about 95, from about 75 to about 80, from about 75 to about 85, from about 75 to about 90, from about 75 to about 95, from about 80 to about 90, from about 80 to about 95, or from about 60 to about 100%.

Other aspects described under the heading 'location and nature of shear thinning material' above with reference to seal assembly 100 are also applicable to seal assemblies 200-600, for example, the presence of multiple compartments or multiple bladders within the seal portion as is described herein. Seal assemblies 200-600 are also able to achieve a tight-fit and a loose-fit as described for other seal assemblies of the invention, and in both cases, are able to form an effective seal with the facial geometry of a user.

Selected Modifications

Figure 21A:
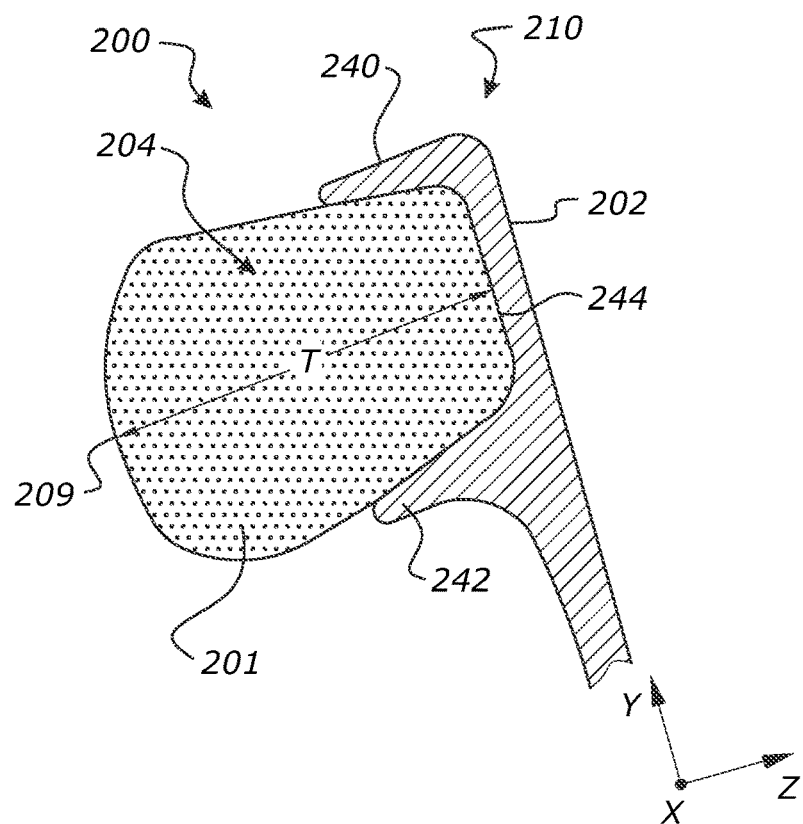
FIGS. 21A and 21B are cross-sectional views of a further embodiment of the invention where the seal portion 204 of the seal assembly 200 comprises support walls 240 and 242.
Figure 21B:
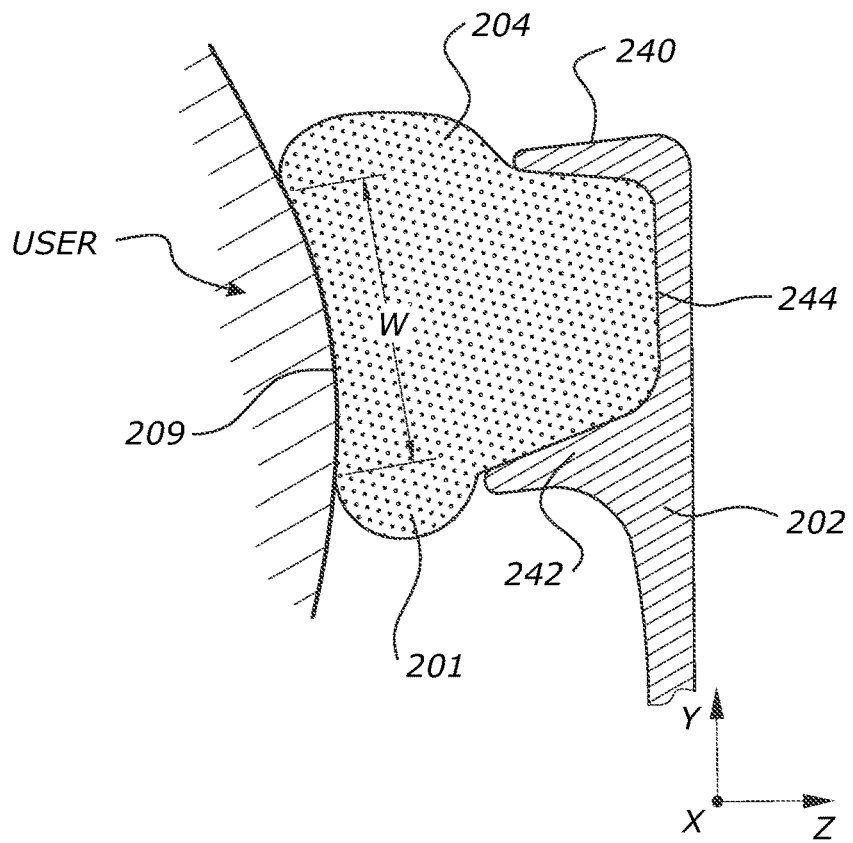
Figure 22A:
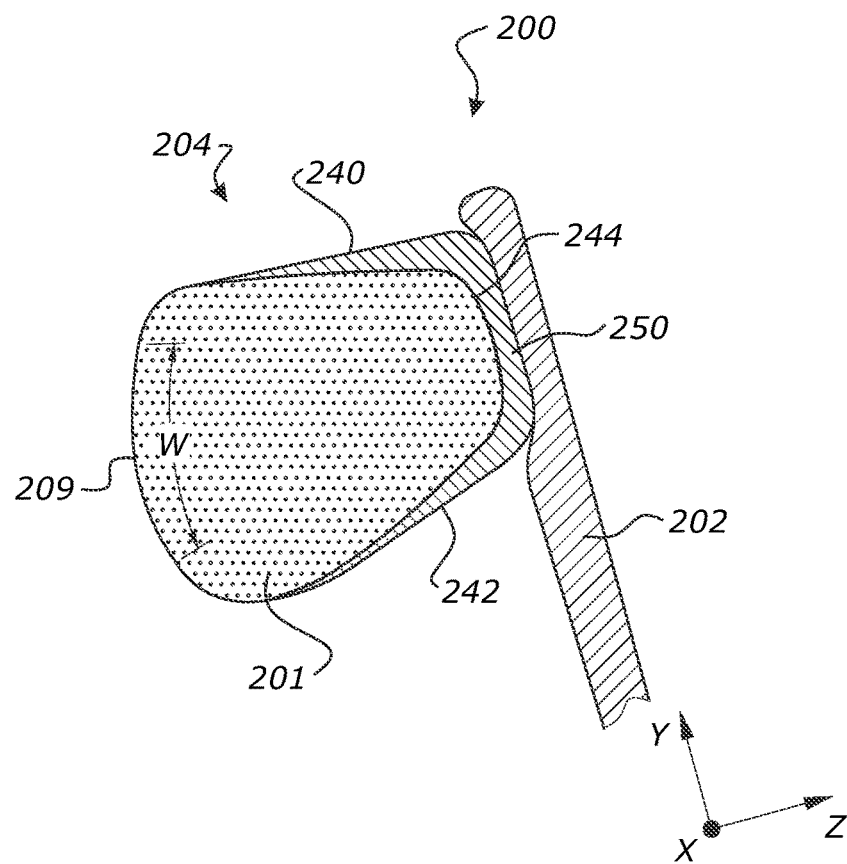
FIGS. 22A and 22B are cross-sectional views of yet another embodiment of the invention where
Figure 22B:
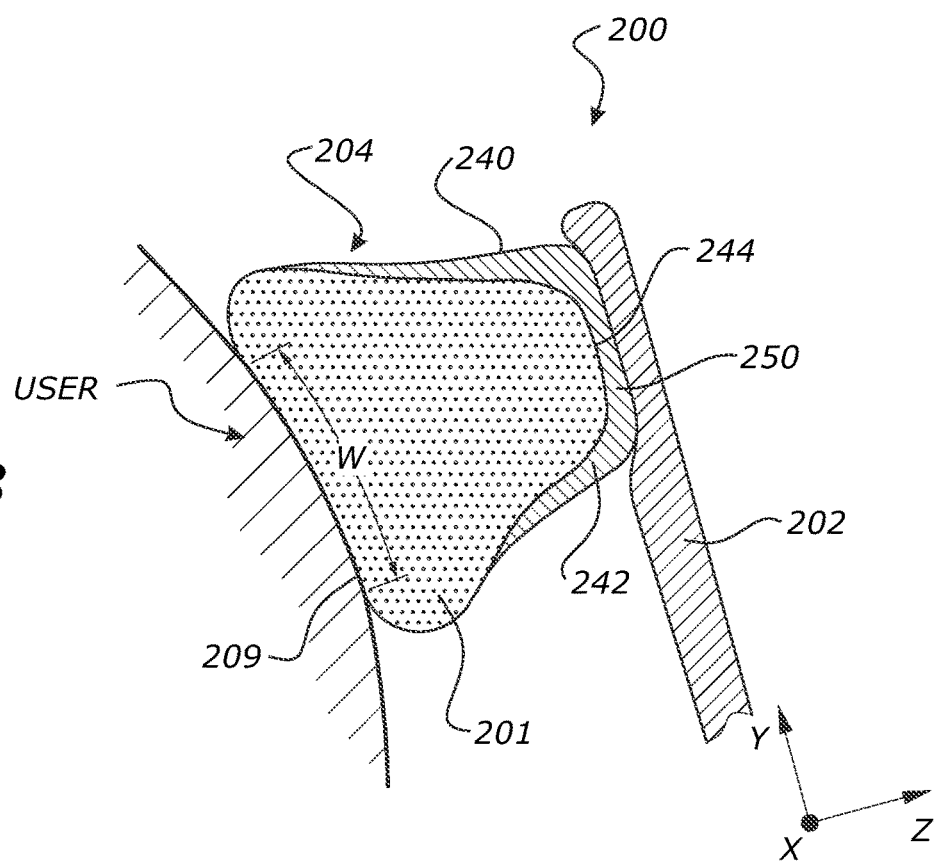

FIGS. 21 and 22 illustrate a simplified view of a modification that may be made to the housing portion of seal assemblies described herein. Using full-face seal assembly 200 as an example only, and with reference to FIGS. 21 and 22, the perimeter portion 210 of the housing portion 202 may include outer support wall 240 and inner support wall 242. The outer and inner support walls 240, 242 can extend around substantially the entirety (FIGS. 22A and 22B) or only a portion of the perimeter 210 of the housing portion 202 (FIGS. 21A and 21B). The outer and inner support walls 240, 242 can be made from the same material as the housing portion 202. Additionally, the outer and inner support walls 240, 242 can extend generally parallel to one another and thus form a channel around the perimeter 210 of the housing portion 202. Disposed between the outer and inner support walls 240, 242, the housing portion may include a connecting surface 244.

With continued reference to FIGS. 21 and 22, in some embodiments the connecting surface 244 may be used with or without the inwardly facing surfaces of the outer support wall and inner support wall 240, 242 to form a connection to the seal portion 204. In the illustrated configuration shown in FIGS. 21 and 22, the outer and inner support walls 240, 242 may extend generally along the thickness T of the seal portion 204. As such, the outer and inner support walls 240, 242 can aid in providing support for the seal portion 204 when the seal portion 204 is conformed against facial geometry of a user.

For example, the outer and inner support walls 240, 242 shown in FIGS. 21 and 22 may reduce or eliminate the likelihood that the seal portion 204 can become completely "bottomed out" or in other words deformed to the point where the thickness T could be reduced to zero or near zero, with virtually little or no shear thinning material 201 between the sealing surface 209 and the connecting surface 244.

Additionally, the outer and inner support walls 240, 242 shown in FIGS. 21 and 22 may help concentrate the "z axis" deformation of the seal portion 204. In other words, in some embodiments the outer and inner walls 240, 242 may resist the widening of the seal portion 204 disposed between the outer and inner walls 240, 242 thereby concentrating more of the expansion of the seal portion 204 and thus the width W of the sealing surface 209, as illustrated in FIG. 21B. As such, the portion of the sealing surface 209 in contact with the skin of the user grows, thereby creating a larger contact patch between the seal portion 204 and the skin of the user.

FIGS. 21A and 21B also illustrate how the sealing surface 209 in the neutral state (FIG. 21A) is re-shaped and oriented to follow a curved shape along an arc (FIG. 21B) that is distorted out of the X-Y plane, into the Z-axis. Additionally, FIGS. 21A and 21B illustrate that the sealing surface 209, when in a neural state (FIG. 21A) may have a convex shape and when in a conformed state pressed up to form a seal with a facial geometry of a user (FIG. 21B) can have a concave shape, thereby providing enhanced conformability.

Further, along the lines discussed above with the manner in which the seal portion 204 enlarged as noted above with regard to FIG. 21B, the enlargement of the sealing surface 209 and the other surrounding portion of the seal portion 204 proximal to the user's face can also help prevent any part of the housing portion 202 from contacting the user's face and causing associated discomfort.

With continued reference to FIGS. 21A and B, the outer and inner support walls 240, 242 can be configured to be a semi-rigid or substantially rigid extension of the housing portion 202. For example, the connecting surface of the seal portion 204 is disposed between the outer and inner walls 240, 242 and thus can act as a retention for the seal portion 204.

FIG. 21B shows the seal portion 204 being deformed from a neutral state, as being pressed against a user's face. As such, the deformation generally occurs outside of the support walls 240, 242.

A modification of the seal assemblies depicted in FIGS. 21A and 21B is shown in FIGS. 22A and 22B. In this modification the seal assembly 200 comprises outer and inner support walls 240, 242 that have a varied thickness along their length.

In some embodiments, for example as shown in FIGS. 22A and 22B with reference to seal assembly 200, the seal assemblies of the invention may comprise a thickened portion 250. The thickened portion may be made from a flexible material, such as silicone, rubber or other materials. In some embodiments, the thickened region 250 may have a higher spring constant than the other portions of the housing, for example the outer and inner support walls 240, 242. In other words, more force is required to deform the thickened region, than the remaining parts of the housing, for example the outer and inner support walls 240, 242. As such, the deformation of the seal portion 204 can be similar to the deformation of the seal portion 204 described above with reference to FIGS. 21A and 21B. In one embodiment housing portion 202 and thickened region 250 may be integrally formed.

With continued reference to FIGS. 21 and 22, and using seal assembly 200 as an example only, in some embodiments the outer and inner support walls 240, 242 may be integrally formed with the bladder of the seal portion 204, which can provide the additional benefit of a smoother, softer transition between the more flexible portion of the outer and inner support walls 240, 242 and the thickened region 250, thereby further preventing user discomfort.

As shown in FIG. 22B, when the seal portion 204 is deformed against the user's face, the support walls 240, 242 can at least partially splay apart as the seal portion 204 is compressed. Such a structure can provide for a more controlled deformation of the seal portion 204. The tapered thicknesses of the support walls 240, 242 can better control where and how deformation occurs, for example, allowing greater deformation of the seal portion 204 in regions proximal to the user's face as compared to the regions proximal to the housing portion 202.

It will be understood by a person skilled in the art that the above-described modifications, for example the presence of outer and inner support walls 240, 242 and/or a thickened region 250 may also be used with other seal assemblies of the invention, for example seal assemblies 300-600.

In some embodiments of any of embodiments 100-600, the seal assemblies may be constructed with only a part of the seal portion comprising a shear thinning material, such as a shear thinning material having a shear thinning index useful herein, such as may be determined according to ASTM E3070-16. For example, shear thinning material may be present only in parts of the seal portion that are proximate to those portions a user's face for which achieving an airtight seal may be more challenging, for example, in the area around the bridge of the nose and the transitions to the adjacent cheek areas.

In some embodiments shear thinning materials may be used in parts of the seal portion that contact areas that are often susceptible to pressure related skin damage resulting from excessive application forces, for example, areas shown in FIGS. 1A and 1B.

In various embodiments seal portions comprising a shear thinning material as described above, may be more effective at deforming to match complicated geometries, for example around the nasal bridge of a user, thus reducing leaks and dispersing application forces more evenly.

In some embodiments, the seal assemblies of the invention may comprise seal portions made up of multiple parts, wherein a first part of the seal portion comprises a shear thinning material, and a second part comprises a traditional seal portion. In some embodiments the seal assemblies may comprise a seal portion comprising a first part and a second part, wherein the first part comprises a shear thinning material and is adapted to contact an area of a patient that is susceptible to pressure related skin damage, and wherein the second part comprises a traditional seal portion (without a shear thinning material) adapted to contact other areas of a patient, that is, areas that are less susceptible to pressure related skin damage. In some embodiments, such a seal assembly may help to reduce the weight of the seal assembly including the headgear of the interface.

In various embodiments of the seal assemblies described above, the housing portion may be strengthened by a frame provided to the housing portion. For example, FIGS. 19, 20A and 20B show a housing portion 502 provided to a frame 530.

In various embodiments the frame (if present) may be made of a number of materials for example any medical grade plastic, for example polycarbonate.

Interfaces Comprising a Seal Assembly and Headgear

In various embodiments the seal assemblies described herein may be used in conjunction with a range of different types of headgear for securing the seal assembly to a target area of a user, for example a user's face, in particular to one or more respiratory orifices of a user. The headgear may be attached either permanently or removably to the housing portion of the seal assembly or to the frame if present.

Figure 23:
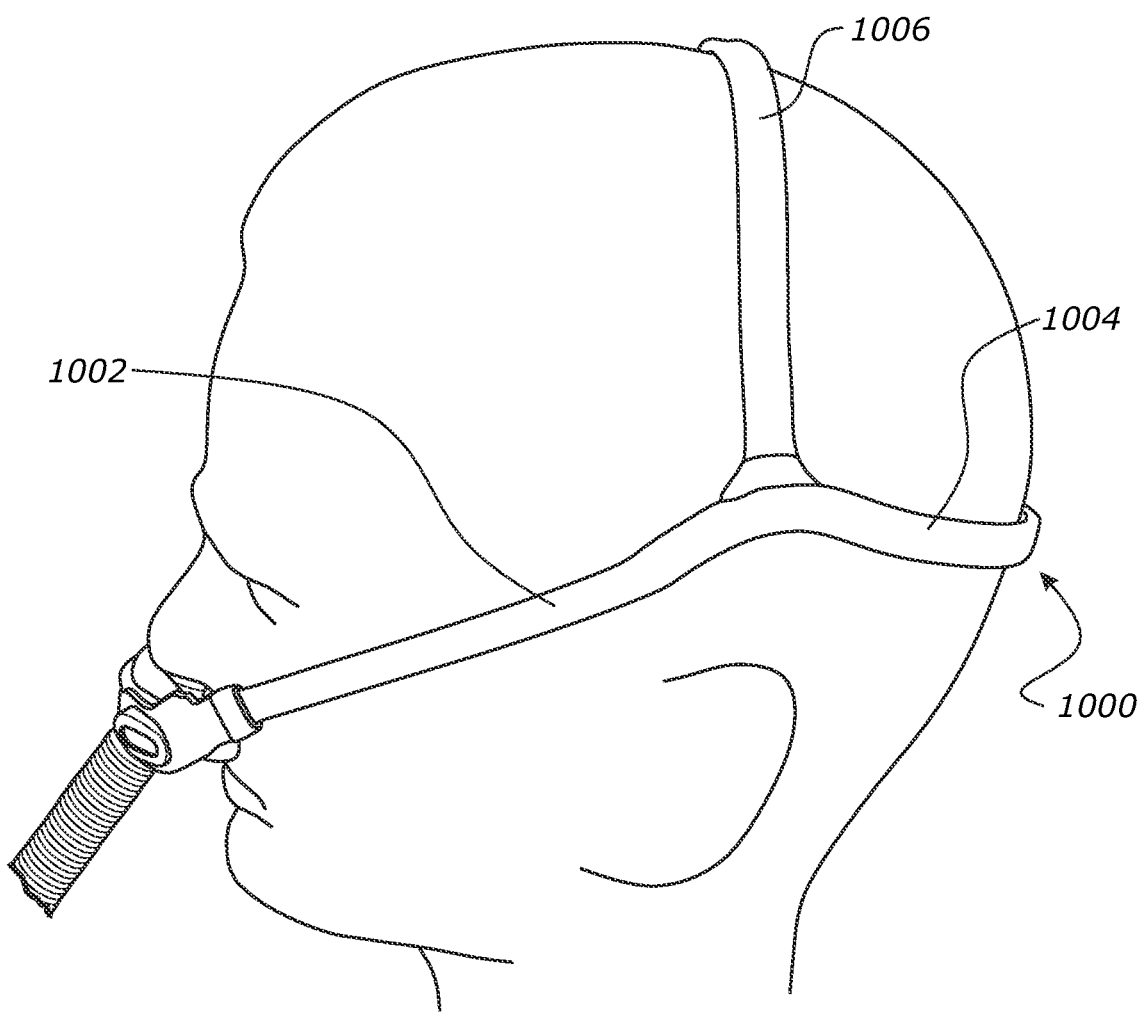
FIG. 23 shows a perspective view of a headgear 1000 that may be used with various embodiments of the invention.

For example, FIG. 23 illustrates a non-limiting exemplary embodiment of a headgear 1000 arrangement that may be used in an interface of the invention. The headgear 1000 may comprise two side straps 1002 (only one shown) connected above and behind the user's ears to a rear strap 1004 configured to extend across the occiput of a user's head. The headgear 1000 may further comprise a top strap 1006 provided to the side straps 1002 and configured to extend across the parietal region of the user's head.

With continued reference to FIG. 23 the side straps 1002 may be permanently or removably connected, for example using hook-and-loop fastener, one or more clips, one or more magnets, a yoke connection, buckles or any other suitable mechanism known in the art, to the housing portion of the seal assembly or to the frame if present.

In some embodiments one or more of the shear thinning materials described herein may be incorporated into the headgear 1000 to be used with a seal assembly. In these embodiments, the parts of the headgear 1000 comprising the shear thinning material may further comprise a volume adjuster as is described herein, that may be the same or different as the volume adjuster in the seal portion of the seal assembly. For example, in some embodiments the volume adjuster may comprise one or more insertable members, for example one or more pistons, configured to be inserted into the bladder to reduce the bladder volume.

Optionally, the headgear 1000 can also include a shape sustaining layer. The shape sustaining layer may be made from a semi-rigid material such that it can provide some structural support to the headgear 1000 when not in use. The shape sustaining layer may minimize the likelihood of the headgear 1000 tangling when it is not applied to a user's head, by keeping the headgear 1000 in a substantially open, three-dimensional shape. It can be advantageous for the headgear 1000 to maintain a substantially open three-dimensional shape as it can help fitting the headgear 1000 and seal assembly of an interface more quickly and more easily.

In some embodiments, the shape sustaining layer may only be included in one or limited parts of the headgear 1000 which benefit from additional structural support. Additionally, including a discontinuous shape sustaining layer throughout the headgear 1000 may allow for the headgear 1000 to conform more readily to the size and shape of different users' heads.

Further, the headgear 1000 can also include a cushioning layer positioned on the inner side headgear and/or the shape sustaining layer so as to provide additional comfort for the user. The cushioning layer may be configured to be in direct contact with the user's head or skin or hair or may be separated from the user's head by a decorative outer layer. In some embodiments the cushioning layer may be made from any soft material such as, but not limited to, foams, textiles, elastomers, and spacer fabrics. The cushioning layer may provide comfort to the user by softening any hard or sharp edges that may be formed by other layers within the headgear 1000. In some embodiments the cushioning layer may be elastic. Providing some elasticity in any of the layers of the headgear can provide an additional benefit of a temporary pre-loading feature during fixation of the interface on a patient's face.

Additionally, as noted above, the headgear 1000 can include a decorative outer layer which can comprise a soft aesthetically pleasing sleeve. In some embodiments, the decorative outer layer may encase the cushioning layer as well, or the cushioning layer may form the face contacting portion of the decorative outer layer. In some embodiments the decorative outer layer may be made from any suitable textile, polymer or other suitable material that is capable of providing a comfortable interface with the user's skin.

A number of examples of seal assemblies and interfaces, and variations and modifications of the seal assemblies and interfaces of the invention have been described with reference to the Figures. The present application contemplates that a respiratory device may incorporate some aspects discussed herein but not other aspects. For example, a respiratory device might incorporate aspects of one or more interfaces described herein while using an arrangement other than that shown in FIG. 23 to secure the seal assembly to a user. All of these variations are considered within the scope of this application.

Although the inventions disclosed herein are described in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure.

It is also contemplated that various combination or subcombinations of the specific features and aspects of the embodiments can be made and still fall within the scope of the inventions.

It should be understood that various features and aspects of the disclosed embodiments can be combined with or substituted for one another in order to form varying modes of the disclosed inventions. Thus, it is intended that the scope of at least some of the present inventions herein disclosed should not be limited by the particular disclosed embodiments described above.

What is claimed is:

1. A seal assembly for a respiratory interface, the seal assembly comprising:
 a seal portion configured to form a seal with at least a portion of a user's face, the seal portion comprising a bladder having an internal volume that contains a shear thinning material; and
 a volume adjuster adapted to adjust the internal volume of the bladder, the volume adjuster comprising at least one insertable member configured to be moved in a first direction to cause a corresponding reduction in the internal volume of the bladder and moved in a second direction to cause a corresponding increase in the internal volume of the bladder.

2. The seal assembly of claim 1, wherein the internal volume of the bladder has an internal resting volume, and the volume adjuster is adapted to reduce the bladder to a volume of less than 100% of the internal resting volume.

3. The seal assembly of claim 1, wherein the volume adjuster comprises two insertable members configured to be inserted into the bladder at spaced apart locations to reduce the internal volume of the bladder.

4. The seal assembly of claim 1, wherein the at least one insertable member is slidable within a channel.

5. The seal assembly of claim 1, wherein the at least one insertable member is adapted to move between a disengaged position in which a substantial portion of the at least one insertable member is outside the bladder and an engaged position in which a substantial portion of the at least one insertable member is inside the bladder.

6. The seal assembly of claim 1, wherein the at least one insertable member has an engagement surface adapted to be engaged by a user to move the at least one insertable member from a disengaged position to an engaged position.

7. The seal assembly of claim 1, the seal assembly further comprising at least one flow path through the seal portion for delivery of respiratory gas to a user.

8. The seal assembly of claim 1, wherein the bladder is formed from a flexible, substantially non-elastic material.

9. The seal assembly of claim 1, wherein the shear thinning material is not an electro-rheological or magneto-rheological fluid.

10. The seal assembly of claim 1, wherein the shear thinning material has an exponential relationship between viscosity and shear rate.

11. The seal assembly of claim 1, wherein the shear thinning material has a shear stress yield threshold.

12. The seal assembly of claim 1, wherein the shear thinning material comprises a Bingham plastic.

13. The seal assembly of claim 1, wherein the shear thinning material comprises an aqueous composition comprising a metal salt or metalloid salt and at least one polyol.

14. The seal assembly of claim 1, wherein the shear thinning material comprises an aqueous composition comprising a metal salt or metalloid salt and at least one polyol, and wherein
 the metal salt or metalloid salt is selected from the group consisting of aluminum hydroxide, calcium carbonate, calcium hydrogen phosphate, silica, zeolite and hydroxyapatite, or a combination of any two or more thereof, and
 at least one polyol is selected from the group consisting of glycerol, sorbitol, xylitol, 1,2-propylene glycol and polyethylene glycol, or a combination of any two or more thereof.

15. The seal assembly of claim 1, wherein the shear thinning material comprises xanthan gum.

* * * * *